(12) United States Patent
Fulton

(10) Patent No.: US 9,561,094 B2
(45) Date of Patent: Feb. 7, 2017

(54) DEVICES AND METHODS FOR TREATING VENOUS DISEASES

(75) Inventor: Richard E. Fulton, Grand Junction, CO (US)

(73) Assignee: Nfinium Vascular Technologies, LLC, Grand Junction, CO (US)

( * ) Notice: Subject to any disclaimer, the term of this patent is extended or adjusted under 35 U.S.C. 154(b) by 70 days.

(21) Appl. No.: 13/190,416

(22) Filed: Jul. 25, 2011

(65) Prior Publication Data

US 2012/0022579 A1    Jan. 26, 2012

Related U.S. Application Data

(60) Provisional application No. 61/400,157, filed on Jul. 23, 2010, provisional application No. 61/400,593, filed on Jul. 30, 2010.

(51) Int. Cl.
| | |
|---|---|
| *A61F 2/01* | (2006.01) |
| *A61B 17/221* | (2006.01) |
| *A61F 2/24* | (2006.01) |
| *A61B 17/3207* | (2006.01) |

(52) U.S. Cl.
CPC ............... *A61F 2/01* (2013.01); *A61B 17/221* (2013.01); *A61F 2/2412* (2013.01); *A61F 2/2418* (2013.01); *A61B 17/3207* (2013.01); *A61B 17/32075* (2013.01); *A61B 2017/2212* (2013.01); *A61B 2017/320716* (2013.01); *A61F 2/013* (2013.01); *A61F 2/2475* (2013.01); *A61F 2002/011* (2013.01); *A61F 2002/016* (2013.01); *A61F 2220/0008* (2013.01); *A61F 2220/0016* (2013.01); *A61F 2230/0006* (2013.01);
(Continued)

(58) Field of Classification Search
CPC ..................... A61B 17/221; A61B 2017/2212; A61B 2002/011; A61B 2250/0067; A61B 2230/0065;A61B 17/3207; A61B 17/32075; A61B 2017/320716; A61F 2/2412; A61F 2/013; A61F 2/2475; A61F 2002/015; A61F 2002/016; A61F 2002/011
USPC ... 606/200, 151, 191, 198, 104; 623/1, 1.23; 604/194; 607/122
See application file for complete search history.

(56) References Cited

U.S. PATENT DOCUMENTS

| | | |
|---|---|---|
| 2,230,226 A | 2/1941 | Auzin |
| 2,259,488 A | 10/1941 | Raiche |
| 3,050,066 A | 8/1962 | Koehn |

(Continued)

FOREIGN PATENT DOCUMENTS

| | | |
|---|---|---|
| EP | 0983749 A2 | 3/2000 |
| EP | 1179321 A2 | 2/2002 |
| EP | 1549229 A2 | 7/2005 |
| EP | 1761298 A2 | 3/2007 |
| EP | 1799128 A2 | 6/2007 |
| EP | 1981413 A2 | 10/2008 |
| EP | 1399089 B1 | 12/2008 |
| EP | 1629784 B1 | 1/2010 |

(Continued)

OTHER PUBLICATIONS

Schmitz-Rode, et al. New device for percutaneous fragmentation of pulmonary emboli. Radiology. Jul. 1991;180(1):135-7.
(Continued)

*Primary Examiner* — Diane Yabut
(74) *Attorney, Agent, or Firm* — Wilson Sonsini Goodrich & Rosati

(57) ABSTRACT

The present invention relates generally to a medical device and method of use, and more specifically to a method and apparatus with coaxial components used to treat venous diseases. The apparatus according to various embodiments operates as an inferior vena cava filter, a clot puller, a clot shredder, and as a prosthetic venous valve.

20 Claims, 8 Drawing Sheets

(52) U.S. Cl.
CPC .......... *A61F 2230/0065* (2013.01); *A61F 2230/0069* (2013.01); *A61F 2250/0067* (2013.01)

(56) References Cited

U.S. PATENT DOCUMENTS

| | | |
|---|---|---|
| 3,540,431 A | 11/1970 | Mobin-Uddin |
| 3,799,172 A | 3/1974 | Szpur |
| 3,831,587 A | 8/1974 | Boyd |
| 3,834,394 A | 9/1974 | Hunter et al. |
| 3,952,747 A | 4/1976 | Kimmell, Jr. |
| 3,978,863 A | 9/1976 | Fettel et al. |
| 3,996,938 A | 12/1976 | Clark, III |
| 4,030,503 A | 6/1977 | Clark, III |
| 4,372,293 A | 2/1983 | Vijil-rosales |
| 4,401,124 A | 8/1983 | Guess et al. |
| 4,425,908 A | 1/1984 | Simon |
| 4,445,892 A | 5/1984 | Hussein et al. |
| 4,494,531 A | 1/1985 | Gianturco |
| 4,573,966 A | 3/1986 | Weikl et al. |
| 4,581,017 A | 4/1986 | Sahota |
| 4,582,061 A | 4/1986 | Fry |
| 4,606,347 A | 8/1986 | Fogarty et al. |
| 4,608,965 A | 9/1986 | Anspach, Jr. et al. |
| 4,611,594 A | 9/1986 | Grayhack et al. |
| 4,621,636 A | 11/1986 | Fogarty |
| 4,646,736 A | 3/1987 | Auth |
| 4,650,466 A | 3/1987 | Luther |
| 4,696,304 A | 9/1987 | Chin |
| 4,727,873 A | 3/1988 | Mobin-uddin |
| 4,762,130 A | 8/1988 | Fogarty et al. |
| 4,793,348 A | 12/1988 | Palmaz |
| 4,794,925 A | 1/1989 | Mori |
| 4,794,928 A | 1/1989 | Kletschka |
| 4,799,495 A | 1/1989 | Hawkins et al. |
| 4,820,270 A | 4/1989 | Hardcastle et al. |
| 4,832,055 A | 5/1989 | Palestrant |
| 4,858,810 A | 8/1989 | Intlekofer |
| 4,869,259 A | 9/1989 | Elkins |
| 4,895,560 A | 1/1990 | Papantonakos |
| 4,921,478 A | 5/1990 | Solano et al. |
| 4,921,484 A | 5/1990 | Hillstead |
| 4,926,858 A | 5/1990 | Gifford, III et al. |
| 4,946,440 A | 8/1990 | Hall |
| 4,977,897 A | 12/1990 | Hurwitz |
| 5,011,488 A | 4/1991 | Ginsburg |
| 5,048,530 A | 9/1991 | Hurwitz |
| 5,059,166 A | 10/1991 | Fischell et al. |
| 5,078,685 A | 1/1992 | Colliver |
| 5,081,997 A | 1/1992 | Bosley, Jr. et al. |
| 5,092,839 A | 3/1992 | Kipperman |
| 5,100,425 A | 3/1992 | Fischell et al. |
| 5,102,415 A | 4/1992 | Guenther et al. |
| 5,108,420 A | 4/1992 | Marks |
| 5,112,347 A | 5/1992 | Taheri |
| 5,116,352 A | 5/1992 | Schnepp-pesch et al. |
| 5,135,484 A | 8/1992 | Wright |
| 5,171,305 A | 12/1992 | Schickling et al. |
| 5,176,659 A | 1/1993 | Mancini |
| 5,183,463 A | 2/1993 | Debbas |
| 5,183,464 A | 2/1993 | Dubrul et al. |
| 5,192,290 A | 3/1993 | Hilal |
| 5,209,727 A | 5/1993 | Radisch, Jr. et al. |
| 5,213,569 A | 5/1993 | Davis et al. |
| 5,221,269 A | 6/1993 | Miller et al. |
| 5,226,909 A | 7/1993 | Evans et al. |
| 5,250,060 A | 10/1993 | Carbo et al. |
| 5,275,611 A | 1/1994 | Behl |
| 5,312,360 A | 5/1994 | Behl |
| 5,328,471 A | 7/1994 | Slepian |
| 5,329,942 A | 7/1994 | Gunther et al. |
| 5,330,484 A | 7/1994 | Gunther et al. |
| 5,334,211 A | 8/1994 | Shiber |
| 5,336,205 A | 8/1994 | Zenzen et al. |
| 5,342,306 A | 8/1994 | Don Michael |
| 5,370,660 A | 12/1994 | Weinstein et al. |
| 5,380,273 A | 1/1995 | Dubrul et al. |
| 5,380,284 A | 1/1995 | Don Michael |
| 5,382,259 A | 1/1995 | Phelps et al. |
| 5,383,466 A | 1/1995 | Partika |
| 5,383,897 A | 1/1995 | Wholey |
| 5,410,093 A | 4/1995 | Dorai |
| 5,419,774 A | 5/1995 | Willard et al. |
| 5,423,799 A | 6/1995 | Shiu |
| 5,431,676 A | 7/1995 | Dubrul et al. |
| 5,437,631 A | 8/1995 | Janzen |
| 5,441,485 A | 8/1995 | Peters |
| 5,443,454 A | 8/1995 | Tanabe et al. |
| 5,454,790 A | 10/1995 | Dubrul |
| 5,456,667 A | 10/1995 | Ham et al. |
| 5,462,529 A | 10/1995 | Simpson et al. |
| 5,483,976 A | 1/1996 | McLaughlin et al. |
| 5,490,521 A | 2/1996 | Davis et al. |
| 5,496,275 A | 3/1996 | Sirhan et al. |
| 5,497,782 A | 3/1996 | Fugoso |
| 5,498,236 A | 3/1996 | Dubrul et al. |
| 5,501,408 A | 3/1996 | Kang et al. |
| 5,518,498 A | 5/1996 | Lindenberg et al. |
| 5,540,658 A | 7/1996 | Evans et al. |
| 5,549,626 A | 8/1996 | Miller et al. |
| 5,556,408 A | 9/1996 | Farhat |
| 5,569,275 A | 10/1996 | Kotula et al. |
| 5,569,277 A | 10/1996 | Evans et al. |
| 5,571,135 A | 11/1996 | Fraser et al. |
| 5,591,204 A | 1/1997 | Janzen et al. |
| 5,606,979 A | 3/1997 | Hodgson |
| 5,611,345 A | 3/1997 | Hibbeln |
| 5,626,614 A | 5/1997 | Hart |
| 5,632,754 A | 5/1997 | Farley et al. |
| 5,643,282 A | 7/1997 | Kieturakis |
| 5,653,684 A | 8/1997 | Laptewicz et al. |
| 5,653,689 A | 8/1997 | Buelna et al. |
| 5,662,671 A | 9/1997 | Barbut et al. |
| 5,662,703 A | 9/1997 | Yurek et al. |
| 5,681,335 A | 10/1997 | Serra et al. |
| 5,683,411 A | 11/1997 | Kavteladze et al. |
| 5,683,451 A | 11/1997 | Lenker et al. |
| 5,695,501 A | 12/1997 | Carol et al. |
| 5,695,507 A | 12/1997 | Auth et al. |
| 5,709,697 A | 1/1998 | Ratcliff et al. |
| 5,709,704 A | 1/1998 | Nott et al. |
| 5,713,848 A | 2/1998 | Dubrul et al. |
| 5,730,733 A | 3/1998 | Mortier et al. |
| 5,733,294 A | 3/1998 | Forber et al. |
| 5,738,652 A | 4/1998 | Boyd et al. |
| 5,749,883 A | 5/1998 | Halpern et al. |
| 5,766,135 A | 6/1998 | Terwilliger |
| 5,766,191 A | 6/1998 | Trerotola |
| 5,766,203 A | 6/1998 | Imran et al. |
| 5,769,795 A | 6/1998 | Terwilliger |
| 5,769,871 A | 6/1998 | Mers Kelly et al. |
| 5,779,672 A | 7/1998 | Dormandy, Jr. |
| 5,792,157 A | 8/1998 | Mische et al. |
| 5,795,308 A | 8/1998 | Russin |
| 5,795,322 A | 8/1998 | Boudewjin |
| 5,797,960 A | 8/1998 | Stevens et al. |
| 5,814,064 A | 9/1998 | Daniel et al. |
| 5,827,324 A | 10/1998 | Cassell et al. |
| 5,833,650 A | 11/1998 | Imran |
| 5,843,022 A | 12/1998 | Willard et al. |
| 5,846,251 A | 12/1998 | Hart |
| 5,851,210 A | 12/1998 | Torossian |
| 5,853,422 A | 12/1998 | Huebsch et al. |
| 5,868,708 A | 2/1999 | Hart et al. |
| 5,897,567 A | 4/1999 | Ressemann et al. |
| 5,904,698 A | 5/1999 | Thomas et al. |
| 5,908,435 A | 6/1999 | Samuels |
| 5,916,235 A | 6/1999 | Guglielmi |
| 5,928,186 A | 7/1999 | Homsma et al. |
| 5,928,260 A | 7/1999 | Chin et al. |
| 5,935,139 A | 8/1999 | Bates |
| 5,947,985 A | 9/1999 | Imran |
| 5,947,995 A | 9/1999 | Samuels |
| 5,954,737 A | 9/1999 | Lee |

(56) References Cited

U.S. PATENT DOCUMENTS

| | | |
|---|---|---|
| 5,972,019 A | 10/1999 | Engelson et al. |
| 5,997,503 A | 12/1999 | Willis et al. |
| 6,001,118 A | 12/1999 | Daniel et al. |
| 6,027,520 A | 2/2000 | Tsugita et al. |
| 6,053,876 A | 4/2000 | Fisher |
| 6,053,900 A | 4/2000 | Brown et al. |
| 6,086,605 A | 7/2000 | Barbut et al. |
| 6,096,053 A | 8/2000 | Bates |
| 6,156,005 A | 12/2000 | Theron et al. |
| 6,161,034 A | 12/2000 | Burbank et al. |
| 6,179,860 B1 | 1/2001 | Fulton, III et al. |
| 6,206,868 B1 | 3/2001 | Parodi |
| 6,217,600 B1 | 4/2001 | Dimatteo |
| 6,221,006 B1 | 4/2001 | Dubrul et al. |
| 6,221,086 B1 | 4/2001 | Forber |
| 6,231,544 B1 | 5/2001 | Tsugita et al. |
| 6,238,412 B1 | 5/2001 | Dubrul et al. |
| 6,258,115 B1 | 7/2001 | Dubrul |
| 6,277,083 B1 | 8/2001 | Eggers et al. |
| 6,287,271 B1 | 9/2001 | Dubrul et al. |
| 6,356,782 B1 | 3/2002 | Sirimanne et al. |
| 6,361,545 B1 | 3/2002 | Macoviak et al. |
| 6,375,634 B1 | 4/2002 | Carroll |
| 6,413,235 B1 | 7/2002 | Parodi |
| 6,443,971 B1 | 9/2002 | Boylan et al. |
| 6,450,989 B2 | 9/2002 | Dubrul et al. |
| 6,485,501 B1 | 11/2002 | Green |
| 6,530,923 B1 | 3/2003 | Dubrul et al. |
| 6,540,768 B1 | 4/2003 | Diaz et al. |
| 6,544,278 B1 | 4/2003 | Vrba et al. |
| 6,602,204 B2 | 8/2003 | Dubrul et al. |
| 6,605,102 B1 | 8/2003 | Mazzocchi et al. |
| 6,626,886 B1 | 9/2003 | Barbut |
| 6,635,068 B1* | 10/2003 | Dubrul et al. .............. 606/200 |
| 6,656,202 B2 | 12/2003 | Papp et al. |
| 6,660,014 B2 | 12/2003 | Demarais et al. |
| 6,695,858 B1 | 2/2004 | Dubrul et al. |
| 6,699,260 B2 | 3/2004 | Dubrul et al. |
| 6,740,094 B2 | 5/2004 | Maitland et al. |
| 6,852,097 B1* | 2/2005 | Fulton, III .............. 604/266 |
| 6,945,977 B2 | 9/2005 | Demarais et al. |
| 6,994,677 B1 | 2/2006 | Buehlmann et al. |
| 7,201,770 B2 | 4/2007 | Johnson et al. |
| 7,220,269 B1 | 5/2007 | Ansel et al. |
| 7,232,432 B2 | 6/2007 | Fulton, III et al. |
| 7,374,561 B2 | 5/2008 | Barbut |
| 7,422,579 B2 | 9/2008 | Wahr et al. |
| 7,534,251 B2 | 5/2009 | Wasdyke |
| 7,569,071 B2 | 8/2009 | Haverkost et al. |
| 7,645,296 B2 | 1/2010 | Theron et al. |
| 7,670,368 B2 | 3/2010 | Hill et al. |
| 7,686,825 B2 | 3/2010 | Hauser et al. |
| 7,780,722 B2 | 8/2010 | Thielen et al. |
| 7,803,171 B1 | 9/2010 | Uflacker |
| 7,867,274 B2 | 1/2011 | Hill et al. |
| 7,951,189 B2 | 5/2011 | Haverkost et al. |
| 7,959,603 B2 | 6/2011 | Wahr et al. |
| 8,366,737 B2 | 2/2013 | Hancock et al. |
| 8,657,849 B2 | 2/2014 | Parker |
| 8,663,273 B2 | 3/2014 | Khairkhahan et al. |
| 8,771,289 B2 | 7/2014 | Mohiuddin et al. |
| 8,777,976 B2 | 7/2014 | Brady et al. |
| 8,784,441 B2 | 7/2014 | Rosenbluth et al. |
| 9,211,396 B2 | 12/2015 | Aboytes |
| 2002/0007130 A1 | 1/2002 | Burbank et al. |
| 2002/0016555 A1 | 2/2002 | Ritchart et al. |
| 2002/0019640 A1 | 2/2002 | McGuckin, Jr. |
| 2002/0022859 A1 | 2/2002 | Hogendijk |
| 2002/0026201 A1 | 2/2002 | Foerster et al. |
| 2002/0045916 A1 | 4/2002 | Gray et al. |
| 2002/0095169 A1 | 7/2002 | Maitland et al. |
| 2002/0165574 A1 | 11/2002 | Ressemann et al. |
| 2002/0165598 A1 | 11/2002 | Wahr et al. |
| 2003/0023204 A1 | 1/2003 | Vo et al. |
| 2003/0083608 A1 | 5/2003 | Evans et al. |
| 2003/0109896 A1 | 6/2003 | Dubrul et al. |
| 2003/0114879 A1 | 6/2003 | Euteneuer et al. |
| 2003/0163158 A1 | 8/2003 | White |
| 2004/0015150 A1 | 1/2004 | Zadno-Azizi |
| 2004/0044391 A1 | 3/2004 | Porter |
| 2004/0153117 A1 | 8/2004 | Clubb et al. |
| 2004/0181237 A1 | 9/2004 | Forde et al. |
| 2004/0199202 A1 | 10/2004 | Dubrul et al. |
| 2004/0236369 A1* | 11/2004 | Dubrul .............. 606/200 |
| 2004/0260332 A1 | 12/2004 | Dubrul et al. |
| 2004/0260333 A1 | 12/2004 | Dubrul et al. |
| 2005/0038447 A1 | 2/2005 | Huffmaster |
| 2005/0187570 A1 | 8/2005 | Nguyen et al. |
| 2005/0277976 A1 | 12/2005 | Galdonik et al. |
| 2006/0047286 A1 | 3/2006 | West |
| 2006/0058836 A1 | 3/2006 | Bose et al. |
| 2006/0200074 A1 | 9/2006 | Zadno-Azizi |
| 2007/0126161 A1 | 6/2007 | Gray et al. |
| 2007/0142858 A1 | 6/2007 | Bates |
| 2007/0233175 A1 | 10/2007 | Zaver et al. |
| 2008/0058800 A1* | 3/2008 | Collins et al. .............. 606/41 |
| 2008/0119888 A1 | 5/2008 | Huffmaster |
| 2010/0030256 A1* | 2/2010 | Dubrul et al. .............. 606/200 |
| 2010/0114113 A1 | 5/2010 | Dubrul et al. |
| 2010/0228281 A1 | 9/2010 | Gilson et al. |
| 2011/0270178 A1 | 11/2011 | Fiorella et al. |
| 2011/0270298 A1 | 11/2011 | Abrams |
| 2012/0316597 A1 | 12/2012 | Fitz et al. |
| 2013/0110152 A1 | 5/2013 | Dubrul et al. |
| 2013/0144326 A1 | 6/2013 | Brady et al. |
| 2013/0310803 A1 | 11/2013 | Morsi |
| 2013/0317534 A1 | 11/2013 | Zhou et al. |
| 2013/0345739 A1 | 12/2013 | Brady et al. |
| 2014/0005712 A1 | 1/2014 | Martin |
| 2014/0039598 A1 | 2/2014 | Sampognaro et al. |
| 2014/0188127 A1 | 7/2014 | Dubrul et al. |
| 2014/0188156 A1 | 7/2014 | Tekulve et al. |
| 2014/0236219 A1 | 8/2014 | Dubrul et al. |
| 2014/0343602 A1 | 11/2014 | Cox et al. |
| 2015/0066075 A1 | 3/2015 | Russell et al. |
| 2015/0112376 A1 | 4/2015 | Molaei et al. |
| 2015/0190141 A1 | 7/2015 | Cragg et al. |
| 2015/0257775 A1 | 9/2015 | Gilvarry et al. |
| 2016/0045202 A1 | 2/2016 | Ferry et al. |
| 2016/0058458 A1 | 3/2016 | Hansen et al. |
| 2016/0074024 A1 | 3/2016 | Scheule |

FOREIGN PATENT DOCUMENTS

| | | |
|---|---|---|
| EP | 2057967 B1 | 1/2013 |
| EP | 2596828 A1 | 5/2013 |
| EP | 2683309 A2 | 1/2014 |
| EP | 2707077 A1 | 3/2014 |
| EP | 2744423 A1 | 6/2014 |
| EP | 2801325 A1 | 11/2014 |
| EP | 2854924 A1 | 4/2015 |
| EP | 2879625 A1 | 6/2015 |
| EP | 2908901 A2 | 8/2015 |
| EP | 2341845 B1 | 1/2016 |
| EP | 2979649 A1 | 2/2016 |
| FR | 2312264 A1 | 12/1976 |
| FR | 2380018 A1 | 9/1978 |
| GB | 2020557 A | 11/1979 |
| JP | H 08-308932 A | 11/1996 |
| JP | H 10-328306 A | 12/1998 |
| JP | 2006-519657 A | 8/2006 |
| WO | WO 80/01343 A1 | 6/1980 |
| WO | WO 80/01353 A1 | 7/1980 |
| WO | WO 94/24946 A1 | 11/1994 |
| WO | WO-9509024 A1 | 4/1995 |
| WO | WO 96/01591 A1 | 1/1996 |
| WO | WO 99/23952 A1 | 5/1999 |
| WO | WO 99/44506 A1 | 9/1999 |
| WO | WO 99/44510 A1 | 9/1999 |
| WO | WO 99/44542 A2 | 9/1999 |
| WO | WO 99/44542 A3 | 11/1999 |
| WO | WO 00/12009 A2 | 3/2000 |
| WO | WO 00/12010 A1 | 3/2000 |
| WO | WO-0149208 A1 | 7/2001 |

(56) References Cited

FOREIGN PATENT DOCUMENTS

| | | |
|---|---|---|
| WO | WO-0197697 A1 | 12/2001 |
| WO | WO 02/055146 A1 | 7/2002 |
| WO | WO 02/087677 A2 | 11/2002 |
| WO | WO-03002028 A2 | 1/2003 |
| WO | WO-2004019791 A2 | 3/2004 |
| WO | WO-2005118050 A2 | 12/2005 |
| WO | WO-2006031410 A2 | 3/2006 |
| WO | WO-2007089897 A2 | 8/2007 |
| WO | WO 2008/010197 A2 | 1/2008 |
| WO | WO 2008/010197 A3 | 4/2008 |
| WO | WO-2008124567 A1 | 10/2008 |
| WO | WO-2010010545 A1 | 1/2010 |
| WO | WO-2012009675 A2 | 1/2012 |
| WO | WO-2012011518 A1 | 1/2012 |
| WO | WO-2012120490 A2 | 9/2012 |
| WO | WO-2012155093 A1 | 11/2012 |
| WO | WO-2013028579 A1 | 2/2013 |
| WO | WO-2013177383 A1 | 11/2013 |
| WO | WO-2014022409 A1 | 2/2014 |
| WO | WO-2014062645 A2 | 4/2014 |
| WO | WO-2014164535 A1 | 10/2014 |
| WO | WO-2014180702 A1 | 11/2014 |
| WO | WO-2015057796 A1 | 4/2015 |
| WO | WO-2016040923 A2 | 3/2016 |
| WO | WO-2016064077 A1 | 4/2016 |

OTHER PUBLICATIONS

Sharafuddin, et al. Current status of percutaneous mechanical thrombectomy. Part I. General principles. J Vasc Intery Radiol. Nov.-Dec. 1997;8(6):911-21.
Office action dated Apr. 6, 2015 for U.S. Appl. No. 12/477,371.
Office action dated May 20, 2014 for U.S. Appl. No. 12/477,371.
Office action dated Jun. 29, 2012 for U.S. Appl. No. 12/477,371.
Office action dated Sep. 27, 2013 for U.S. Appl. No. 12/477,371.
Office action dated Nov. 8, 2011 for U.S. Appl. No. 12/477,371.
Office Action for U.S. Appl. No. 10/747,813 mailed on Jan. 10, 2008.
Office Action for U.S. Appl. No. 10/747,813 mailed on Sep. 19, 2007.
Office Action for U.S. Appl. No. 10/747,813 mailed on Jul. 26, 2007.
Office Action for U.S. Appl. No. 10/765,564 mailed on Oct. 9, 2007.
Office Action for U.S. Appl. No. 10/866,980 mailed on Oct. 5, 2007.
Supplementary European Search Report mailed Jul. 23, 2008—EP Application No. 04759873.5-2310; filed Apr. 15, 2004.
Velocimed, "Proxis, Embolic Protection System", http://www.velocimed.com/proxis.htm (visited Feb. 6, 2004), 4pp., (2003).
U.S. Appl. No. 14/554,348, filed Nov. 26, 2014, Fulton.
U.S. Appl. No. 14/645,830, filed Mar. 12, 2015, Fulton.
Final Office Action for U.S. Appl. No. 13/725,871 Mailed on May 21, 2014.
Notice of allowance dated Aug. 21, 2015 for U.S. Appl. No. 13/725,871.
Office action dated Apr. 6, 2015 for U.S. Appl. No. 13/725,871.
Office action dated May 4, 2015 for U.S. Appl. No. 14/201,371.
Office action dated Aug. 5, 2015 for U.S. Appl. No. 14/554,348.
Office action dated Aug. 5, 2015 for U.S. Appl. No. 14/645,830.
Office action dated Nov. 20, 2014 for U.S. Appl. No. 14/201,371.
Office action dated Nov. 28, 2014 for U.S. Appl. No. 13/725,871.
Office Action for U.S. Appl. No. 13/725,871 Mailed on Jul. 15, 2014.
Office Action for U.S. Appl. No. 13/725,871 Mailed on Sep. 5, 2013.

* cited by examiner

DEVICES AND METHODS FOR TREATING VENOUS DISEASES

CROSS REFERENCE TO RELATED APPLICATIONS

This application claims the benefit of U.S. Provisional Patent Application No. 61/400,157, entitled "DEVICE AND METHOD FOR TREATING A TARGET SITE IN A VASCULAR CHANNEL," filed on Jul. 23, 2010, and U.S. Provisional Patent Application No. 61/400,593, entitled "DEVICES AND METHODS OF TREATING VENOUS DISEASE," filed on Jul. 30, 2010, the entire disclosure of each of which is incorporated by reference herein. In addition, the present application cross-references, but does not claim priority to, U.S. patent application Ser. No. 13/111,924 filed May 19, 2011, the entire content of which is incorporated herein by reference in its entirety for at least the purposes of enablement and written description.

FIELD OF THE INVENTION

This disclosure relates generally to a medical device and method of use, and more specifically to a method and apparatus with coaxial components used to treat venous diseases.

BACKGROUND OF THE INVENTION

Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart, it will be pumped into the lungs and may cause a blockage in the pulmonary arteries. A blockage of this type in the lungs will interfere with the oxygenation of the blood causing shock or death.

In the case of venous disease, there are estimated to be over 2 million cases of deep venous thrombosis (DVT) in the U.S. each year. Only about 700,000 are diagnosed, and approximately 200,000 people die of pulmonary embolism, a complication of DVT, causing it to be the third leading cause of death in the U.S., more than breast cancer and AIDS combined. Sixty to seventy percent of patients with DVT eventually experience post thrombotic syndrome (PTS) as a result primarily of damage to the venous valves secondary from the cellular response and overgrowth because of the thrombus. Recurrent DVT will affect a large percentage of those who suffer from the initial episode, further compounding the problem. Therefore, millions of patients will suffer from the acute and chronic problems and health risks posed by DVT.

Thrombosis and atherosclerosis are common ailments which occur in humans and which result from the deposition of thrombus and clot on the walls of blood vessels. When hardened, such deposits are commonly referred to as plaque. Such deposits are most common in the peripheral blood vessels that feed the limbs of the human body and the coronary arteries which feed the heart. Stasis, incompetent valves, and trauma in the venous circulation cause thrombosis, particularly occurring as a deep vein thrombosis in the peripheral vasculature. When such deposits build-up in localized regions of the blood vessel, they can restrict blood flow and cause a serious health risk.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels requires anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

The human venous system in the lower extremities contains a number of one-way valves that function in allowing forward (antegrade) blood flow to the right atrium of the heart while preventing reverse (retrograde) flow to the feet. Using the muscle action of the calf to pump the blood, or the "peripheral heart," the body is able to overcome gravitational forces to maintain blood flow back to the heart. The valves thus prevent blood from pooling in the lower extremities. Physiologically functioning valves are capable of withstanding very high proximal pressure gradients with minimal leakage, and can open at very low distal pressure gradients. However, for many patients, venous function is severely compromised by chronic venous disease (CVD), caused by Chronic Venous Insufficiency (CVI). Many times, CVI is a result of PTS caused by DVT events described above. Over seven million Americans suffer from CVI, a painful and debilitating disease that affects the superficial and deep veins of the legs. Problems associated with CVI include varicose veins, bleeding, ulcerations, severe swelling, deep vein thrombosis, and pulmonary embolism, which may lead to death.

In the venous system, there is also proliferative overgrowth of cellular material at anastomotic sites of the veins with arteries or grafts in the case of dialysis grafts and other surgeries. Most importantly, there is cellular ingrowth of smooth muscle cells into venous valves and the walls of veins after DVT, especially if the thrombus is not cleared quickly. This proliferative cellular response has some similarities to the cellular response that occurs in arteries. The venous valves are particularly affected by deep venous thrombosis and by the eventual cellular response which evolves into a tough and thickened tissue, and the valves become stiff and non-compliant causing them to become incompetent and allowing venous reflux to develop. The ongoing reflux results in venous hypertension, dilated veins, and a plethora of symptoms, including swelling of the lower leg, heaviness, pain, skin discoloration, and even skin ulcers. Collectively, the symptom complex occurring after episodes of DVT and caused mainly by the incompetent venous valves has been referred to as the Post Thrombotic Syndrome (PTS.) Strategies have been employed to remove the venous thrombosis early, by mechanical catheters and pharmacomechanical (mechanical catheters and lytic agents) treatments, and are generally successful and the incidence of PTS is much less than if treated by non invasive means. However, venous reflux still occurs in some of these patients, probably the result of residual thrombus on the valves after the majority of thrombus has been removed and the resulting cellular proliferation that ensues. The cellular ingrowth is a complicated series of events resulting in smooth muscle infiltration, collagen deposition, and fibroblast proliferation, amongst other features that renders the valve leaflet enlarged, stiff, and frequently fused to the vessel wall incapable of function or even being repaired.

The current methods of treating venous diseases including DVT and its complications, notably pulmonary embolism and PTS, are much less than satisfactory for several reasons. The most common method of treating DVT is to administer Heparin, an anticoagulant which does not dissolve the clot, but prevents additional clot from forming. Ninety-five percent of patients treated for DVT are currently treated with Heparin. Heparin administration is convenient and fairly easily done, although it can be expensive. This method relies on the body's inherent thrombolytic processes to dissolve the clot. The main problem with Heparin administration, however, is that all of the clot does not dissolve or it does not dissolve very quickly, and there is resultant residual clot and damage to the venous valves which will lead to PTS. Several studies have documented that there is a lesser incidence of PTS when the thrombus is removed early on in the course of DVT, before the valves are damaged, and that the incidence of recurrent DVT is lessened when the thrombus is removed early on.

In an effort to remove the thrombus early and prevent recurrent DVT and PTS, devices and methods have been invented to remove the thrombus. Initially, in the early 1980's systemic thrombolysis was attempted with a thrombolytic drug. While this method was partially successful, the incidence of bleeding intracranially and in the gastrointestinal (GI) tract was unacceptable. Later, in approximately 1990, a method of catheter directed thrombolysis was developed in which the thrombolytic drug was infused directly into the thrombus. This worked, but the bleeding complications prevented widespread adoption. Around 2000 or so, a procedure termed pharmacomechanical thrombolysis was utilized in which the catheter mechanically agitated the thrombus while the lytic agent was being infused. Again, the bleeding complications were a deterrent to use and even the mechanical action along with the lytic drug did not remove all of the thrombus in most cases. Subsequently, "isolated" pharmacomechanical thrombectomy was developed in which the lytic drug is contained within a section of the vein that is being treated, and most of the lytic drug does not enter the systemic circulation. This was an improvement, and the bleeding complications are lessened. These devices, however, are expensive and carry some risk to the patient, including bleeding, and are frequently not successful in removing all of the thrombus. In fact, the clot is removed completely in the minority of patients and only partially in others. This sometimes necessitates continuing the lytic therapy overnight or for several days in the intensive care unit which is expensive and adds the extra risk of systemic exposure to the lytic agent with subsequent bleeding. The continued lytic therapy raises the potential for bleeding in the GI tract, brain, and elsewhere. Hence, the added cost of the drug and the ICU monitoring and the added risk of protracted exposure to higher levels of the lytic drug is not only problematic to those patients treated in this manner, but they are also a deterrent to other patients even having the procedure which may help them avoid the long term sequelae of aggressive interventional therapy for DVT.

The main reason for subjecting the patient to the additional expense and risk of protracted lytic infusion is that the thrombolytic and thrombectomy devices designed to treat the thrombus within the veins do not remove all of the thrombus. It is well known and accepted in the medical field that these prior art devices only remove or dissolve acute thrombus. The subacute or chronic thrombus which is frequently present is resistant to thrombolysis and thrombectomy. The development of DVT is usually a slow progressive process, and the patient does not really know, and it cannot be determined with any degree of certainty, when the DVT began and, hence, how old the thrombus is, whether acute, subacute, or chronic. Therefore the treating physicians really don't know or have the means to determine if the thrombolytic and thrombectomy devices available to them will work or not. This unknown is a deterrent for using an invasive, potentially dangerous, and very expensive method that may help the patient, but may not. This unknown prevents many patients from receiving aggressive therapy that may be beneficial to them. Both the lack of success of the prior art devices and the fact that many patients are not treated because of this unknown leaves the patient with residual thrombus which demands further costly treatment methods and increases the risk of valvular damage which predisposes the patient to develop recurrent DVT, chronic venous insufficiency and PTS later. There is a need to provide devices and methods that will rid the patient of all of the thrombus, including the subacute and chronic thrombus that prevents adequate treatment in many cases.

Traditionally, pulmonary embolization may be prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patient's vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may be accessed through the jugular vein, located in the patient's neck.

Once placed inside a blood vessel, a thrombus filter acts to catch and hold blood clots. The flow of blood around the captured clots allows the body's lysing process to dissolve the clots.

The walls of the blood vessels are lined with a thin inner membrane or intima. When the securing/anchoring portions of a thrombus filter puncture this inner membrane, the body responds to a puncture of the intima with a process known in the art as neointimal hyperplasia. As a result, the punctured area of inner membrane is overgrown with a number of new cells. The securing portions of the thrombus filter are typically encapsulated with new cell growth (neointimal hyperplasia). Because the portions of the filter contacting the blood vessel wall become fixed in this way, it is impractical to remove many prior art filters percutaneously after they have been in place for more than two weeks.

There are a number of situations in which it may be desirable for a physician to remove a thrombus filter. If the physician determines that more effective filtering would occur with a thrombus filter in a different position, the physician may remove the original filter from its present positions and deploy a new filter in a new position. If the physician determines that the risk of blood clots forming is no longer present, it may be desirable to remove the thrombus filter completely. Thrombus filters are often used in conjunction with anticoagulation drugs. At some point, the physician may desire to discontinue the use of anticoagulation drugs. The physician may also want to remove the thrombus filter in conjunction with discontinuing the anticoagulation drugs. The removal of the thrombus filter from the patient eliminates any possibility that a complete occlusion will occur at the thrombus filter site. The removal of the thrombus filter also eliminates any possibility that the thrombus filter will become loose and migrate within the blood vessel. A loose thrombus filter is undesirable because it may migrate to a dangerous or life threatening position.

For a general background on thrombus filter technology and some of the tools and apparatus used involving thrombus filters, see U.S. Pat. No. 6,217,600 issued to DiMatteo on Apr. 17, 2001 ("DiMatteo"), the entire disclosure of which is incorporated herein by reference in its entirety.

Conventional implantable thrombus filters (also known as blood filters and/or IVC filters) employing a variety of geometries are known. Many are generally basket or cone shaped in order to provide adequate clot-trapping area while permitting sufficient blood flow. Also known are filters formed of various loops of wire, including some designed to partially deform the vessel wall in which they are implanted. Vena cava filters commonly include a core portion from which a plurality of wires radiate outwardly. The wires serve to filter clots from blood flowing through the vein. Various hook-like projections, barbs and the like have been suggested for use in holding the filter in place once the delivery catheter has been withdrawn.

Some traditional vena cava filters include the Vena Tech-LGM vena cava filter, the Bird's Nest vena cava filter, and the Simon-Nitinol vena cava filter. The Vena Tech-LGM filter is a conical filter made from a Phynox alloy, with longitudinal stabilizing legs in addition to the intraluminal cone. The Bird's Nest filter is a "nest" of stainless steel wire which is wound into the vena cava, while the Simon Nitinol filter is a two-stage filter made from nickel-titanium (NiTi) alloy with a conical lower section and a petal-shaped upper section. The TrapEase is a filter laser cut from a single tube of nitinol material and is formed with a symmetric double-basket configuration providing two levels of clot trapping.

Although vascular filters are widely used for capturing emboli in blood vessels, existing filter configurations suffer from a variety of shortcomings that limit their effectiveness. In one shortcoming, vascular filters are susceptible to clogging with embolic material. When a filter becomes partially or totally clogged, the flow of blood through the vessel may be substantially reduced or stopped completely. When this occurs, serious complications can arise and therefore the patient must be treated immediately to restore adequate blood flow. Because of the potential for clogging, existing vascular filters are typically manufactured with relatively large pores or gaps such that only large emboli, such as those with diameters of 7 mm or greater, are captured. The large pore size is necessary for reducing the likelihood of clogging due to smaller particles. Unfortunately, in certain cases, the passage of smaller emboli may still be capable of causing a pulmonary embolism or stroke. Accordingly, physicians and filter manufacturers are required to balance the risk of clogging against the risk of pulmonary embolism and/or stroke.

Traditional indications for filters are patients with deep venous thrombosis, and with a contraindication for anticoagulation, or patients with large floating clots in the iliac veins or IVC, with an imminent risk of embolism. Additional contraindications are young patients or patients with a transient problem that may cause PE not requiring a permanent filter. However, one important problem with many available intravascular filters in use is the non-retrievability of the devices, because while penetration of the retaining hooks of the filter into the lumen of the IVC is necessary for the proper securing of the device, in extreme cases and over time, over-penetration may impinge upon adjacent organs, leading to serious or even fatal complications. Further, with time the filter will be integrated into the aortic wall, making it unretrievable without causing significant damage to the vessel wall, particularly at the body of the basket. Accordingly, a vena cava filter capable of temporary deployment is desired to provide rapid protection against pulmonary embolism. However, as the condition producing blood clots is successfully treated, it may be desired to remove the filter from the vena cava.

Catheter-based mechanical thrombectomy devices provide an alternative treatment method for removing blood clots from a patient's vasculature. Thrombectomy devices are typically used for removing a thrombus that has formed in a blood vessel and has occluded the flow of blood.

See U.S. Pat. No. 7,803,171 issued to Uflacker on Sep. 28, 2010 ("Uflacker") for a general background on thrombus filter technology and some of the tools and apparatus used involving thrombus filters, the entire disclosure of which is incorporated herein by reference in its entirety.

Some attempts have been made to develop thrombus filters that are retrievable and accurately positioned. For example, see U.S. Pat. No. 7,534,251 issued to WasDyke on May 19, 2009 ("WasDyke") which discloses a retrievable vena cava filter of multiple elongated filter legs each having a hook portion configured to releasably secure the filter to the wall of a vessel, and an expandable member releasably connected to the filter. The filter legs may be biased to expand from a substantially straight configuration to an outswept, conical-shaped configuration when deployed in the vessel. The expandable member may include a plurality of securing members configured to pierce and secure the expandable member to the vessel wall. In some embodiments, the expandable member may comprise a bendable member interconnected to several tubular members. In other embodiments, the expandable member may comprise a coiled wire. In use, the expandable member may be utilized to compress the filter legs against the vessel wall. The entire disclosure of WasDyke is incorporated herein by reference in its entirety.

U.S. Pat. No. 4,793,348 issued to Palmaz on Dec. 27, 1988 ("Palmaz") discloses a vena cava filter for preventing migration of lower extremity venous clots into the pulmonary circulation. The Palmaz filter comprises a tubular body, the wall of which is partitioned by a slot pattern into a latticework rendering the tubular body radially expandable; a head piece, having a threaded receiving hole, circumferentially affixed to the distal end of said tubular body; and a plurality of tines affixed in substantially uniform circumferential spacing about the proximal end of said tubular body. In a filter intended for femoral vein introduction into the vena cava, the tines are elongated appendages having hooked terminal ends. In a filter intended for jugular vein introduction, the tines are short spikes. The filter is delivered to the inferior vena cava by catheter means introduced through a vein sheath positioned in the femoral or jugular vein. After location within the caval lumen, the tubular body of the filter is expanded by a balloon catheter contained within the lumen of the filter, thereby rendering the lattice-work wall surface of the tubular body into a filtering network mesh and affixing the expanded filter within the vena cava. After deployment of the expanded filter within the vena cava, the catheter means is withdrawn. The entire disclosure of Palmaz is incorporated herein by reference in its entirety.

U.S. Pat. No. 4,832,055 issued to Palestrant on May 23, 1989 ("Palestrant") discloses a blood clot filter which includes a central core wire extending along a central longitudinal axis and surrounded by a number of peripheral wires evenly spaced about the central core wire. A first connector connects the peripheral wires together at one end of the central core wire at a first fixed connection point. A second connector connects the peripheral wires together at a second connection point spaced apart from the first connection point, the second connection point surrounding the central core wire and being slidably secured thereto. The blood clot filter includes a one-way lock device permitting the second connector to slide along the central core wire toward the first fixed connector from a first position remote from the first connector to a second position proximate the first connector. However, the lock device prevents the second connector from returning from the second proximate position back to the first remote position. The portions of the peripheral wires extending between the first and second connectors initially extend generally along the central core wire. As the second connector is advanced from the first remote position to the second proximate position, the portions of the peripheral wires extending between the first and second connectors move radially away from the central core wire to a deployed position for forming a filter mesh. The entire disclosure of Palestrant is incorporated herein by reference in its entirety.

U.S. Pat. No. 4,727,873 issued to Mobin-Uddin on Mar. 1, 1988 ("Mobin-Uddin") discloses an embolus trap comprising an expansible article which is inserted in its collapsed condition in a passageway and which then opens and secures itself. The Mobin-Uddin device comprises a central hollow column carrying preferably two or more tiers spaced therealong of radially extending elongated filaments, pairs of which are connected at their outer ends to form loops. Each tier includes two or more such loops and the loops of one tier are positioned circumferentially between the loops of the next adjoining tier. At the outside ends, the filaments are formed into outwardly extending hooks backed by offsets, the latter limiting the penetration of the hooks into the wall of a passageway in which the device is implanted. The filaments are preferably made of metal wire or other filament with sufficient spring to permit them to be folded back against the central column while the device is inserted into a passageway and then, when released, to assume a radially-extended position within the passageway forcing their hooked ends against the passage wall. The device is inserted into a vein by a catheter of plastic tubing having a tubular capsule at its distal end containing the device in its collapsed condition. In the capsule, the filaments are forced against the central column and are relatively straight. When the embolus trap is ejected, its filaments spring outwardly in the vein tending to assume their semi-lunar curvature. A wire guide extends through the hollow central column of the device and out beyond the capsule. The wire guide has a flexible J-tip at its outer end which facilitates maneuvering and prevents securing in the wall of the vein. A hollow push rod which fits over the wire allows the catheter to eject the embolus trap from the capsule so that it travels along the wire guide to its destination. For maneuvering the capsule in place, a different type of hollow rod is provided which will not eject the embolus trap from the capsule. The entire disclosure of Mobin-Uddin is incorporated herein by reference in its entirety.

U.S. Pat. No. 6,258,115 issued to Dubrul ("Dubrul I") describes a stent of varying porosity for use in vessels with bifurcations or side branches. The stent allows for scaffolding of the stenotic area but still allows for flow into the side branches. A distal protection system is also described. Also, Dubrul I discloses a procedure-oriented system for carotid stenting which reduces or eliminates the stroke potential during stent placement by positioning a fragment filteritrap/occluder downstream (distally) from where the stent is disposed within a bifurcated blood vessel such as the common carotid artery. The Dubrul I device includes both a single lumen, multi-porous stent and a bifurcated stent, both of which are operable for stenting the common carotid artery at its point of bifurcation. However, the Dubrul I device is designed for use against blood flow with the most open end on the proximal end and not optimized for use with blood flow with the most open end on the distal end.

U.S. Pat. No. 6,238,412 issued to Dubrul et al. on May 29, 2001 ("Dubrul II"), U.S. Pat. No. 6,695,858 issued to Dubrul et al. on Feb. 24, 2004 ("Dubrul III"), and U.S. Pat. No. 6,221,006 issued to Dubrul et al. on Apr. 24, 2001 ("Dubrul IV"), describe a catheter device for removal of a blockage in a passageway, such as a dialysis graft or in a body passageway. The devices of Dubrul II, III and IV include a traditional funnel-like catheter for reception and aspiration of the blockage and an occlusion engaging element supported on a wire that extends through the catheter. The devices include a braid device that expands against the blood vessel wall to stabilize the catheter and to prevent the occlusion from passing around the outside of the device; blood flow is also prevented from passing through the device.

U.S. Pat. No. 6,699,260 issued to Dubrul et al. on Mar. 2, 2004 ("Dubrul V") describes a catheter device for removal of a blockage in a body passageway fitted with a multi-wing malecot expansion device. Similar to Dubrul II, III and IV, the Dubrul V device entirely blocks blood flow, and the targeted blockage, from passing around or through the device. Further, U.S. Pat. Pub. No. 2010/0114113 to Dubrul et al. published May 6, 2010 ("Dubrul VI") discloses a catheter device for occlusion removal that blocks blood flow.

U.S. Pat. Pub. No. 2004/0260333 to Dubrul et al. published on Dec. 23, 2004 ("Dubrul VII") and U.S. Pat. Pub. No. 2010/0030256 to Dubrul et al. published on Feb. 4, 2010 ("Dubrul VIII") describe a collection of funnel catheters, catheter/dilator assemblies, occluders, and associated methods which either entirely block blood flow or do not allow a controlled, predictable adjustment of allowed blood flow.

The entire disclosures of each of Dubrul I through Dubrul VIII are incorporated herein by reference in their entireties.

The prior art thrombus filter techniques or technologies do not provide a minimal-trauma device that enables predictable and reliable positioning, readily allow repositioning, are easily inserted and retracted, capable of removing all thrombus, including subacute and chronic thrombus. Also, traditional thrombus filters techniques or technologies do not allow pulling or moving of thrombus and/or shredding thrombus.

A variety of methods and devices have been developed for treating thrombosis and atherosclerosis in the coronary and peripheral vasculature, as well as in implanted grafts and fistulas. Such devices and techniques attempt to filter, capture, pull and/or shred thrombus. Techniques include surgical procedures, such as coronary artery bypass grafting, and minimally invasive procedures, such as angioplasty, atherectomy, transmyocardial revasculaturization, and the like. Techniques generally described as "thrombectomy" have been developed. Thrombectomy generally refers to procedures for the removal of relatively soft thrombus and clot from the vasculature. Removal is usually achieved by mechanically disrupting the clot, optionally with the introduction of thrombolytic agents. The disrupted thrombus or clot is then withdrawn through a catheter, typically with a vacuum or mechanical transport device.

Thrombectomy generally differs from angioplasty and atherectomy in the type of occlusive material which is being treated and in the desire to avoid damage to the blood vessel wall. The material removed in most thrombectomy procedures is relatively soft, such as the clot formed in deep vein thrombosis, and is usually not hardened plaque of the type treated by angioplasty in the coronary vasculature. Moreover, it is usually an objective of thrombectomy procedures to have minimum or no deleterious interaction with the blood vessel wall. Ideally, the clot will be disrupted and pulled away from the blood vessel wall with no harmful effect on the wall itself.

While successful thrombectomy procedures have been achieved, most have required comprise between complete removal of the thrombosis and minimum injury to the blood vessel wall. While more aggressive thrombectomy procedures employing rotating blades can be very effective at thrombus removal, they present a significant risk of injury to the blood vessel wall. Alternatively, those which rely primarily on vacuum extraction, together with minimum disruption of the thrombus, often fail to achieve sufficient thrombus removal.

For example, U.S. Pat. No. 6,660,014 issued to Demarais on Dec. 9, 2003 ("Demarais I") provides apparatus, systems, methods, and kits for removing occlusive material from body lumens. Demarais discloses a macerator for breaking up or "disrupting" the thrombus, clot, or other occlusive material, where the macerator is positioned to minimize or prevent contact with and reduce or eliminate the potential for injury to the luminal wall. The device comprises a catheter for removing the occlusive material from the body lumen. The catheter comprises a catheter body having a proximal end, a distal end, and a lumen therethrough. A radially expansible positioning cage is disposed on the catheter body near its distal end, and a macerator is disposed within the expansible positioning cage. The macerator is configured to disrupt occlusive material within the cage when the cage is expanded against the luminal wall. The macerator is typically a rotating element, such as a helical or other shaped wire which engages and disrupts the occlusive material. Usually, the disrupted material will also be drawn into the catheter body lumen. Alternatively, the disrupted thrombus can be captured, in whole or in part, by a second catheter usually introduced downstream from the first catheter with the macerator. The second catheter may also comprise a macerator and, in some instances, the two catheters can be similar or identical. In all cases, the disrupted thrombus may be removed through the catheter lumen by aspiration using an external vacuum source and/or a mechanical pump. U.S. Pat. No. 6,945,977 issued to Demarais on Sep. 20, 2005 ("Demarais II") provides additional embodiments of the devices and methods of use to that of Demarais I. Both Demarais I and Demarais II are incorporated herein by reference in their entireties.

U.S. Pat. No. 7,686,825 issued to Hauser on Mar. 20, 2010 ("Hauser") provides a vascular filter device adapted for capturing and breaking down embolic material from the blood. The Hauser device generally comprises a filter body sized for deployment in a blood vessel and an agitation member movably coupled to the filter body. During use, movement of the agitation member acts to break apart particles captured within the filter body. To reduce the possibility of filter migration, the filter body may be provided with anchoring elements for engagement with an inner wall of the blood vessel. The anchoring elements may comprise penetrating tips, barbs, hooks or any other structure configured to engage the inner wall. In another variation, the filter device may be supported by a stent structure that expands for engagement with the inner wall.

The venous system of the legs uses valves and muscles as part of the body's pumping mechanism to return blood to the heart. Venous valves create one way flow to prevent blood from flowing away from the heart. When valves fail, blood can pool in the lower legs, resulting in swelling and ulcers of the leg. The absence of functioning venous valves can lead to chronic venous insufficiency.

The presence of CVI results from damaged (incompetent) one-way vein valves in leg veins. These valves normally allow forward flow of blood to the heart, and prevent blood from pooling at the feet. However, incompetent valves allow reflux of blood, causing clinical problems. There are few effective clinical therapies for treating CVI other than compression stockings and elevating the leg. Vein valve transplantation is a surgical option for treatment. However, it is often difficult to find suitable donor valves. Very few prosthetic valves developed in the past have demonstrated sufficient clinical or mechanical functionality. Persistent problems include thrombus formation, leaking valves, and valves that do not open at physiologic pressure gradient. There is a rather uniform problem of fibrin deposition on the foreign substance constituting the prosthetic valve. There has yet to be a prosthetic venous valve developed that has demonstrated the necessary functional performance for operating satisfactorily in human physiologic conditions. While various designs have been pursued in the past, many such designs possess shortcomings that prevent them from being a sufficiently functional design.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site.

Prosthetic valves can be transplanted into the venous system, but current devices are not successful enough to see widespread usage. One reason for this is the very high percentage of prosthetic valves reported with leaflet functional failures. These failures have been blamed primarily on improper sizing and tilted deployment of the prosthetic valve. In addition, a great number of leaflets of the prosthetic valves ultimately become fused to the vein wall.

A typical traditional prosthetic venous valve is provided in U.S. Pat. No. 7,569,071 issued to Haverkost et al. on Aug. 4, 2009 ("Haverkost I") which discloses venous valve frames, venous valves that utilize the venous valve frames, and methods for forming and using the venous valve frame and the venous valve. Various embodiments can be used to replace and/or augment an incompetent valve in a body lumen. Embodiments of the venous valve include a venous valve frame and valve leaflets that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs. U.S. Pat. No. 7,951,189 issued to Haverkost et al. on May 31, 2011 ("Haverkost II") provides additional embodiments of the devices and methods of use to that of Haverkost I. Haverkost I and Haverkost II are incorporated herein by reference in their entireties.

U.S. Pat. No. 7,670,368 issued to Hill et al. ("Hill I") on Mar. 2, 2010 discloses an apparatus, system, and method for valve replacement or augmentation. The apparatus can include a valve that can be used to replace or augment an incompetent valve in a body lumen. Embodiments of the valve can include a frame and cover that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs. U.S. Pat. No. 7,867,274 issued to Hill et al. on Jan. 11, 2011 ("Hill II") provides additional embodiments of the devices and methods of use to that of Hill I. Hill I and Hill II are incorporated herein by reference in their entireties.

U.S. Pat. No. 7,780,722 issued to Thielen et al. ("Thielen") on Aug. 24, 2010 provides a venous valve with a frame and a cover on the frame for unidirectional flow of a liquid through the valve quite similar to that of Hill I and Hill II. Thielen is incorporated herein by reference in its entirety.

Some attempts have been made to develop venous devices useful and adaptable for multiple applications, see U.S. Pat. No. 5,632,754 issued to Farley et al. on May 27, 1997 ("Farley"), the entire disclosure of which is incorporated herein by reference in its entirety.

Typically, the stability of the catheter tip is problematic and critical to the medical procedure. In many cases a "guide" catheter is inserted and the tip is placed within or near the orifice of the vessel intended to be treated. See for example U.S. Pat. No. 5,947,995 issued to Samuels on Sep. 7, 1999 ("Samuels"), the entire disclosure of which is incorporated herein by reference in its entirety.

For a general background on stenting and guiding catheters, see U.S. Pat. No. 7,645,296 issued to Theron et al. on Jan. 12, 2010 ("Theron"), the entire disclosure of which is incorporated herein by reference in its entirety.

Several devices have been used to place a filtering device into the inferior vena cava using a transvenous route, commonly originating from the right jugular vein or from either femoral vein. For example, the method disclosed in U.S. Pat. No. 3,834,394 to Hunter, et al., ("Hunter") uses a detachable balloon which is delivered to the inferior vena cava at the end of a catheter. The balloon and catheter are inserted into one of the veins in the neck using a surgical incision and passed to the lower inferior vena cava where the balloon is inflated. Once detached, the balloon occludes the inferior vena cava entirely, thereby preventing any flow of blood or blood clots to the heart. While insertion of this device avoids major abdominal surgery, it still requires a small surgical procedure to be performed in order to expose a neck vein. The balloon occludes the inferior vena cava completely, resulting in swelling of the lower extremities until collateral circulation develops around the balloon. With time, these collateral channels may become large enough to permit life threatening emboli to pass to the lung. The entire disclosure of Hunter is incorporated herein by reference in its entirety.

Another device for preventing pulmonary embolism but which does not require total occlusion of the inferior vena cava is an implantable cone-shaped filter device consisting of six spokes with sharpened points at the end and connected together at the other end by a central hub. A thin membrane with 4 mm holes covers the device. The umbrella-like device is folded into a cylindrical capsule connected to the end of a catheter. This device is described in U.S. Pat. No. 3,540,431, to Mobin-Uddin ("Mobin-Uddin"). This device also requires a surgical cutdown on a major right neck vein for access to the venous system. The device and delivery capsule are positioned in the inferior vena cava and released by pushing the device out of the capsule. While the device acts as an efficient filter, approximately 60% of patients using the Mobin-Uddin filter develop occlusion of the inferior vena cava, sometimes resulting in severe swelling of the legs. Furthermore, instances of migration of the filter to the heart have been reported; such instances present a high mortality risk. The entire disclosure of Mobin-Uddin is incorporated herein by reference in its entirety.

U.S. Pat. No. 3,952,747, to Kimmel ("Kimmel"), discloses a blood vessel filter and filter insertion instrument which overcome some of the disadvantages of the previous two devices. The Kimmel patent describes a device which may be inserted either from the jugular or femoral approach using a surgical exposure of a major vein. The conical shaped device consists of six strands of wire each connected to a hub at one end and having recurved hooks on the other end. The device is loaded into a cylindrical delivery capsule which is connected to a catheter. The delivery capsule measures 6 mm in diameter and 5 cm in length. Because of its size, a surgical exposure of the vein is necessary for introduction of the delivery capsule into the vascular system. More recently, the delivery capsule has been introduced into the vascular system through a large catheter using angiographic techniques. However, this technique has been shown to significantly injure the vein at the introduction site. Sometimes it may not be possible to pass the capsule from below through tortuous pelvic veins into the inferior vena cava because of the inflexibility of the capsule. The filter engages the wall of the vein at one end and therefore often tilts to one side. It is very difficult to deliver the filter in a manner that maintains the longitudinal axis of the filter centered along the longitudinal axis of the vena cava. A tilted filter has been shown to be less efficient at capturing blood clots. Migration of the filter has not been a problem. The entire disclosure of Kimmel is incorporated herein by reference in its entirety.

Another method of preventing pulmonary emboli from reaching the lungs is a device disclosed in U.S. Pat. No. 4,425,908, to Simon ("Simon"). This device uses the thermal shape memory properties of Nitinol to deploy the filter following delivery. The filter consists of seven wires banded at one end and also in the middle. The wires between these two points form a predetermined filter mesh derived from the thermal memory. The free-ends of the wires form anchoring points which radially engage the inferior vena cava. The device may be inserted through a jugular or femoral vein approach using standard angiographic catheters. The device relies on the thermal shape memory properties of the Nitinol wire to form an effective filter following delivery. The entire disclosure of Simon is incorporated herein by reference in its entirety.

U.S. Pat. No. 4,494,531, to Gianturco ("Gianturco"), also discloses a blood vessel filter which can be inserted through angiographic catheters. The device consists of a number of strands of wire which are interconnected and wadded together to form a curly wire mesh. The filter includes a number of projections which serve as an anchoring means for anchoring the filter at a suitable body location within the inferior vena cava. Problems with the device include migration and demonstration invitro of filtering inefficiency. The random nature of the filtering mesh makes it difficult to assess the overall efficacy. Perforation of the anchoring limbs through the vena cava has also been described. The entire disclosure of Gianturco is incorporated herein by reference in its entirety.

The use of the above devices can be cumbersome, time-consuming and expensive. Furthermore, these devices do not adequately capture emboli in the blood or remove all thrombus, such as subacute and chronic thrombus. Rather, these devices are typically used to remove a thrombus that has formed within a vessel. In certain cases, these devices may actually produce emboli and cause a stroke or PE. Still further, the contact surfaces or fluid pressures of these mechanical thrombectomy devices may produce a variety of undesirable side effects, such as endothelial denudation and hemolysis. These devices are difficult to position and, in the case of venous valves, unreliable and generally ineffective. Therefore, an urgent need exists for minimal trauma devices and methods for capturing and/or completely removing blood clots from a patient's vasculature and for safely and effectively inserting prosthetic venous valves into a patient's vasculature. The present invention addresses these needs.

The use of the instant inventions and methods are, in the case of venous disease, designed to treat DVT by removing acute, subacute, and chronic thrombus, preventing pulmonary emboli, removing pulmonary emboli, preventing the smooth muscle cell migration and population into the valvular structure which causes valvular incompetence, repairing damaged veins and venous valves, and percutaneously placing prosthetic venous valves.

SUMMARY OF THE INVENTION

Certain embodiments of the present disclosure relate to a medical device and method of use, and more specifically to a method and apparatus with coaxial components used to treat venous diseases. The devices are comprised generally of tubular members configured with an outer sheath or tube, an inner sheath or tube, and an securing element that may be configured at least as an inferior vena cava filter, a clot shredder, a clot puller, and a venous valve. The device may be precisely, reliably, and safely positioned. Other embodiments and alternatives to this device are described in greater detail below.

The present invention is advantageous in a number of respects. In particular, the present invention provides for effective removal of the occlusive material from the body lumen. Such removal is effective in both achieving a high degree of removal and minimizing the amount of material which is released into the body lumen. This is a particular advantage in treatment of the vasculature where the release of emboli can be a serious risk to the patient. The present invention achieves such effective removal with minimum risk of injury to the luminal wall.

While the present invention is particularly suitable for the removal of thrombus and clot from the vasculature (to include thrombus or clots that are spread or distributed in the vasculature as well as isolated thrombus or clots and combinations thereof), it will also find use in other body lumens, such as the ureter, urethra, fallopian tubes, bile duct, and intestines.

As used in this disclosure, the terms "venous disease treatment device," "venous treatment device," and "device" all refer to one or more embodiments of the invention.

By way of providing additional background, context, and to further satisfy the written description requirements of 35 U.S.C. §112, the following references are incorporated by reference in their entireties for the express purpose of explaining the nature of the venous disease treatment device technology and surgical procedures in which such devices are used and to further describe the various tools and other apparatus commonly associated therewith: U.S. Pat. No. 5,078,685 issued to Colliver; U.S. Pat. No. 6,238,412 issued to Dubrul et al.; U.S. Pat. No. 6,695,858 issued to Dubrul et al.; U.S. Pat. No. 6,699,260 issued to Dubrul et al.; U.S. Pat. No. 6,635,068 issued to Dubrul et al.; U.S. Pat. No. 5,916,235 issued to Guglielmi; U.S. Pat. Pub. No. 2010/0114113 to Dubrul et al.; U.S. Pat. Pub. No. 2004/0260333 to Dubrul et al.; U.S. Pat. Pub. No. 2010/0030256 to Dubrul et al; U.S. Pat. Pub. No. 2010/0228281 to Gilson et al; WO 2008/010197 to Gilson; and U.S. Pat. No. 6,852,097 to Fulton.

Additionally, the following references are also incorporated by reference in their entireties for the express purpose of explaining the nature of the venous disease treatment device technology and surgical procedures in which such devices are used and to further describe the various tools and other apparatus commonly associated therewith: U.S. Pat. No. 5,904,698 describes a catheter having an expansible mesh with a blade or electrode for shearing obstructive material which penetrates the mesh when the mesh is expanded in a blood vessel. Other catheters having expansible meshes, cages, and/or shearing elements are described in U.S. Pat. Nos. 5,972,019; 5,954,737; 5,795,322; 5,766,191; 5,556,408; 5,501,408; 5,330,484; 5,116,352; and 5,410,093; and WO 96/01591. Catheters with helical blades and/or Archimedes screws for disrupting and/or transporting clot and thrombus are described in U.S. Pat. Nos. 5,947,985; 5,695,501; 5,681,335; 5,569,277; 5,569,275; 5,334,211; and 5,226,909. Catheters having expansible filters at their distal ends are described in U.S. Pat. No. 4,926,858 and PCT publications WO 99/44542 and WO 99/44510. Other catheters of interest for performing thrombectomy and other procedures are described in U.S. Pat. Nos. 5,928,186; 5,695,507; 5,423,799; 5,419,774; 4,762,130; 4,646,736; and 4,621,636. Techniques for performing thrombectomy are described in Sharafudin and Hicks (1997) JVIR 8: 911-921 and Schmitz-Rode and Gunthar (1991) Radiology 180: 135-137.

According to varying embodiments described herein, the present invention is directed to the use of a device comprised generally of tubular members configured with an outer sheath or tube, an inner sheath or tube, and a securing element that may be configured at least as an inferior vena cava filter, a clot shredder, a clot puller, and a venous valve. The device may be precisely, reliably, and safely positioned. Although the present invention is directed towards applications involving venous diseases, the invention may be used in any medical application where it is important to position a medical device and manipulate elements in a confined space. Also, the present invention may be used in primary surgery, as well as in revision surgery in which a follow-up procedure is being performed in an area that has previously been subject to one or more surgeries. Further, the invention may be used in any application where material is to be controlled, manipulated, captured or shredded with precision to a confined area where access is restricted to include surgical procedures, repair of installed or uninstalled mechanical or electrical devices, and arming or disarming of explosive devices. Although many embodiments and examples discuss use of the device within a human, the device and methods of use may be used in any animal. Also, although many embodiments and examples describe use of the device within a blood vessel or other human vessel, the device and methods of use may be used in any body channel of a human or animal. In addition, although blood is referenced frequently as the fluid involved with the device, any fluid present in a body channel is applicable to the invention.

It is one purpose of the invention disclosed to describe a device and method that would administer a non proliferative drug before, during, or after the lytic process that would inhibit the cellular proliferation that eventually causes the valvular damage and the resulting valvular incompetence that leads to PTS. This is likely to be most effective after most of the thrombus has been removed, dissolved, or allowed to be resorbed by the body's inherent processes. The prevention of the valvular damage is dependent upon rapid removal of the thrombus, but the addition of an anti proliferative agent has the potential to even further diminish the incidence of PTS. The device may be equipped with proximal and distal occluders to contain an instilled antiproliferative agent, such as paclitaxel, placed into vein for a period of time, and then to aspirate the agent, or just release the agent into the systemic circulation. This could be accomplished by using a clot puller like device to occlude one end of the segment to be treated and a catheter with an occlusive means, such as a balloon or funnel tip, to occlude the other end of the segment and infusing the antiproliferative agent between the occluded proximal and distal ends. The antiproliferative agent would bathe the area for several minutes or more and then be withdrawn by aspiration through the catheter while releasing the clot puller like occluder at the other end of the segment, so that backflow of blood in the syringe would assure one that all of the lytic agent was removed.

Briefly, in one preferred embodiment of the invention, the invention devices are comprised generally of tubular members configured with an outer sheath or tube, an inner sheath or tube, and a securing element that may be configured at least as an inferior vena cava filter, a clot shredder, a clot puller, and a venous valve.

According to various embodiments of the present disclosure, one aspect of the invention is to provide a procedural inferior vena cava filter, one that is attached to a guide wire and utilized for only a few hours to a few days, then collapsed and retrieved by the same guide wire. It is similar in construction to the distal occluder described elsewhere in this document, comprised of two coaxial shafts moveable in relationship to each other. The inner shaft may be a solid wire and the outer coaxial shaft may be a tubular structure which fits over the inner shaft. A tubular braid is attached to the ends of the shafts such that the braid essentially is continuous in plane and shape with the outer tubular shaft when the inner shaft is advanced distally to its limit. When the inner shaft is withdrawn in respect to the outer shaft, the braid deforms from a tubular shape to a football like shape or even a plate like shape. In fact, there are any number of shapes that may be achieved between the tubular collapsed shape of the braid with the inner member or shaft advanced and the plate like shape with the inner shaft withdrawn maximally. The number of wires of the braid, the size of the wires, the pics per inch, longitudinal lay ins and other braiding techniques may be varied to achieve the desired features of an IVC filter which include, but are not limited to: 1) trapping most, if not all, thrombi to prevent new or recurrent PE; 2) nonthrombogenic and able to maintain caval patency; 3) made of a biocompatible material that is durable and noncorrosive; 4) of a shape and structural integrity maintainable for a long time; 5) a delivery system of a low profile and allowing easy placement; 6) clot trapping reasonably effective even if filter deployment is suboptimal; 7) not migrating after deployment; 8) minimal to no perforation of the IVC; 8) nonferromagnetic to allow MRI to be performed after its placement; and 9) retrievable.

The filter of the current invention substantially addresses these criteria, as the material will likely be nitinol which is nonferromagnetic, biocompatible, durable, noncorrosive, structurally strong, amongst other features. The design substantially allows for blood flow in the IVC with trapping of most emboli. Being guide wire based, it naturally has a low profile for easy placement and removal. If initial deployment is suboptimal, the device can easily be collapsed and redeployed by the simple movement of the inner shaft relative to the outer shaft. The filter of the current invention will not migrate as it is attached to a guide wire and, in the preferred embodiment, not designed to be detached. There are no hooks or barbs to hold it in place, so perforation of the IVC is not of a concern.

In one embodiment, the venous disease treatment device comprises an outer sheath coaxially placed over an inner sheath. The two sheaths are moveable relative to the each other serving to expand and collapse the expansile braid portion. When the braid is expanded, the inner sheath is advanced out from and away from the outer sheath, causing the expansile braid portion to controllably engage the vessel wall. In this manner, the device may be very deliberately and accurately positioned, or re-positioned, against a vessel wall within a patient. Herein the terms "expansile braid" and "mesh braid" and "braid" all reference the device braid portion. The device braid portion may be self-expanding or it may be controlled by actuator sheaths. The braid expands to the vessel wall and stabilizes the device distal tip by contacting the vessel wall, essentially securing the device to the vessel wall by a gentle annular force.

Further, in this embodiment, the device braid portion is attached to the outer or exterior of the outer sheath. The device would be inserted and removed into a patient in the undeployed configuration. When the braid portion is deployed or extended, it may take a shape akin to a football shape. The braid portion is extended or deployed by withdrawing the inner shaft or sheath with respect to the outer shaft or sheath. Other shapes for the partially or fully deployed or expended braid may be designed to include, but not be limited to, oblong, spherical, toroid, and generally any substantially three-dimensional shape that substantially restricts passage of material, such as thrombus, from passing such a shape along or inside the vessel wall. A spacer may be incorporated to limit the deformity of the braid portion to a particular shape and/or to prevent the braid from deforming into a plate-like and/or planar shape. The deployed shape may also be substantially two-dimensional (e.g. a plate-like shape) if such a shape substantially restricts passage of material, such as thrombus, from passing along or inside the vessel wall.

The braid portion configuration to include, but not be limited to, the braid portion density, strand thickness, adhesiveness, and characteristics that influence the porosity or flow through the braid portion can be varied to ensure adequate blood flow, but adequate trapping of venous emboli.

When the device of this embodiment is used during a thrombolytic procedure, the device would be left in place for hours or even days after the procedure. Alternatively, the device may be used when there is no thrombolytic procedure, but as protection against emboli in patients who cannot be anticoagulated because of surgery or other circumstances. In the configuration of the device discussed immediately above, the braid portion remains attached to the device outer sheath and thus would have to eventually be removed.

Other embodiments of the venous disease treatment device include a clot/thrombus puller and a clot/thrombus shredder, as well as an occluder. More specifically, variations in the braid portion configuration to include, but not be limited to, the braid portion density, strand thickness, adhesiveness, diameter of strands, and other characteristics that influence the porosity or flow through the braid portion, and/or the ability of the braid to capture and/or move a clot or thrombus. For example, a braid portion that does not allow substantial flow, that is, a braid portion that is substantially impermeable, would be employed as an occluder that may be used to occlude venous branches, for example. An occluder stops or blocks most, if not all, blood flow. Alternatively, a braid portion configured with braids that allow larger clot particles to pass (than, for example, an IVC filter configuration) and that, when pulled into a thrombus would tend to substantially cut or break-up the thrombus, would be deemed a clot/thrombus shredder.

An embodiment of the device for use as a clot shredder would generally have braid portion comprising a lower density of strands. In such a clot shredder embodiment, the thrombus fragments may be removed through a catheter or may be further dissolved with a thrombolytic catheter. The clot shredder device is similar to the filter described above, but sized appropriately to the particular vessel. It is comprised of an inner and outer shaft as above with a tubular braid attached to the distal portions of both. When the inner shaft is withdrawn with respect to the outer shaft, the braid deforms initially into a football shape and then into a plate like shape. For this application, it is desirable to have fewer wires or members of the braid and fewer pics per inch, or less of a braid density. This would cause the device, when pulled though a clot, to cut it similar to a cheese slicer rather than pull it along the vessel. In use, the device would be utilized on clot or thrombus that was resistant to being lysed completely by a lytic agent. It may be advantageous for the clot to have been softened by the lytic process before the clot shredder is employed. The braid of the device is placed on one side of the clot and the shaft components on the opposite side. The braid is deployed into a football or plate like shape and the device is withdrawn toward a catheter with a balloon or a funnel occluder on or near its tip, as described elsewhere. While it is likely that the clot will be withdrawn with the device for a distance toward the catheter, the resistance and occlusion produced by the balloon or funnel catheter will prevent further propagation of the clot with the device. At this point, continued traction and withdrawal of the device with respect to the clot and the occluding catheter will cause excessive pressure on the clot causing the wires to cut through the clot and fragment the clot into several to many pieces, essentially shredding the clot. This will allow the lytic agent to further act on the smaller fragments or more likely for the smaller fragments to be aspirated easily through the catheter. This could be augmented by exchanging the clot shredder for a clot puller.

Further, a clot puller device is different than the IVC filter configuration and/or the clot shredder configuration principally because of the characteristics of the braid portion. The clot puller is constructed very similarly to the clot shredder with an inner and outer sleeve and an expansile segment, but with means to pull the clot along rather than shred it. Those means may include more wires or members, more pics per inch, a denser braid density, or even an elastomeric covering of the braid to more effectively pull the clot into the catheter. In the clot puller embodiment of the device, the components and the actions are similar to the clot shredder with movement of the inner shaft or sheath with respect to the outer shaft or sheath deforming the expansile braid portion segment into a shape that engages the vessel wall. The expansile braid portion segment may have a denser braid density (than the IVC embodiment and/or the clot shredder embodiment) and optionally an elastomeric covering to better pull clot material along the interior of the vessel and into a catheter, for example, for removal.

In another embodiment of the venous disease treatment device, an additional feature, an extended proximal portion, is provided. In this embodiment, the device comprises a distal tip configured with device braid portion. When deployed, the braid portion imparts a minimal but effective level of axial force against the surrounding vessel of a patient so as to stabilize the device. The venous disease treatment device comprises an outer sheath coaxially placed over an inner sheath. The two sheaths are moveable relative to the each other serving to expand and collapse the expansile braid portion. When the braid is expanded, the inner sheath is withdrawn out from and away from the outer sheath causing the expansile braid portion to controllably engage the vessel wall. In this manner, the device may be very deliberately and accurately positioned, or re-positioned, against a vessel wall within a patient. The device braid portion may be self-expanding or it may be controlled by actuator sheaths. The braid expands to the vessel wall and stabilizes the device distal tip by contacting the vessel wall, essentially securing the device to the vessel wall by a gentle annular force.

The device braid portion is attached to the outer or exterior of the outer sheath. The device would be inserted and removed into a patient in the undeployed configuration. When the braid portion is deployed or extended, it may take a shape akin to a football shape. The braid portion is extended or deployed by withdrawing the inner shaft or sheath with respect to the outer shaft or sheath.

In another embodiment of the invention, the device comprises a particularly extended proximal portion and a particularly extended distal portion. The extended distal portion may be configured so as to comprise a distal tip that attaches to the inner sheath or, instead, may be a member attached to the distal tip, such as a wire. In this embodiment, the length of the extended distal portion is preferably between 50-400 cm in length, more preferably between 70-180 cm in length, and most preferably between 90-150 cm in length. The length of the extended distal portion is such that the device be manipulated from the popliteal venotomy and from the jugular venotomy.

In another embodiment of the device, the deployed or extended braid portion is detachable from the device and, thus, would be permanently left in the patient. The detachable feature is enabled by any of several means to include temporary or transient bonding/attachment of the braid portion to the outer sheath and temporary or transient bonding/attachment of the inner sheath to the device distal tip such that a first movement of the inner sheath away from distal tip serves to deploy the braid portion, and continued second movement of the inner sheath away from distal tip serves to sever the attachment/bonding of the inner sheath to the distal tip, thereby detaching the deployed braid portion. When employing the device in this manner, the remaining components of the device are then withdrawn from the patient, and the deployed braided portion would remain in the patient to serve, for example, as an IVC filter. The means to enable the detachable feature include, but are not limited to, interference fits of the braid portion and one or both of the outer sheath and/or to the device distal tip, separation as induced by differential thermal properties of the components and/or by connective components (not shown) that lose adhesive properties upon heating (for example, as caused by continued placement with a patient and/or against a vessel wall). Means may also be enabled through magnetic, electrical, mechanical, or other typical methods of providing temporary connections between components.

To maintain a football like shape, which is advantageous for an IVC filter, the device contains a means for preventing the proximal and distal ends of the braid from approximating each other. Otherwise, the ends of the braid would collapse and essentially touch each other, causing the braid to deform into a plate like configuration, which would not be the most optimum shape for an IVC filter. This means may simply be a tubular spacer on the inner wire or shaft, or there may be a restricting means within the braid to prevent it from collapsing onto itself completely. Other solutions to this dilemma are certainly possible and included herein by reference. In this alternative embodiment, the filter, when detached, would obviously become a permanent filter. This alternative embodiment may be used as a procedural or temporary filter initially and then, if warranted by clinical parameters or other factors, could be detached and become a permanent filter if clinical concerns or other factors warrant a permanent type filter.

In a preferred method of use, the filter is inserted via the internal jugular vein through a standard angiographic catheter, although it may be inserted through the femoral or other vein. A point just below the lowermost renal vein is usually chosen and the filter device of the current invention is advanced out of the catheter and positioned properly at this location. There may be a radiopaque marker on the distal aspect of the outer shaft just proximal to the transition to the tubular braid to help in positioning the device precisely.

The inner shaft is withdrawn with respect to the outer shaft causing the braid component to deform into the desired shape which will be more or less a football type shape. The outer shaft will be held in place with the radiopaque marker remaining stationary. This will cause the distal end of the inner shaft to retract when the inner shaft is withdrawn, but the cephalic portion of the deployed filter will not move, allowing precise positioning of this device. This one feature overcomes the difficulty with other prior art devices with precise positioning. If, for some reason, the position of the deployed filter device is not as precise as the operator desires, the inner shaft is simply advanced, collapsing the braid into a tubular shape, the device repositioned, and the braid is redeployed at the new location by withdrawing the inner shaft. There may be a spacer or a restrictive device placed on the inner shaft or at another location that prevents the braid from deforming completely into a plate like configuration. Otherwise, if too much tension or retractive force is placed upon the inner shaft, the braid would continue to deform from the relaxed tubular shape to the desired football shape and then to an undesired plate like shape.

In this preferred embodiment, the expanded filter remains attached to the inner and outer shafts. It may be left in place for several hours while a procedure of venous thrombolysis is being performed or left in place for several days to weeks, and then withdrawn. It may be repositioned from one to several times over an extended period of several days to weeks to prevent incorporation into the vena cava wall. To withdraw the device, one simply advances the inner shaft with respect to the outer shaft and collapses the braid into a tubular shape, then removes the device from the body. If there is clot within the filter, as determined by imaging before removal, one may choose to remove the filter device through a funnel shaped catheter that will accept the incompletely collapsed braid and the clot or embolus within it. This overcomes a major problem with current retrievable IVC filters in that they frequently cannot be successfully retrieved because there is clot within the filter, or because they cannot be engaged with a retrieval wire or device. Many of these "temporary" IVC filters are simply left in place because they cannot be successfully removed, therefore they become permanent filters. To obscure the issue, some have been renamed "optional" filters, indicating that they may be temporary, but if they cannot be removed, there is the "option" of leaving them in place. There really is no option other than to leave them in place. Since the current invention remains attached to the wire, there will be no problem engaging it, as it is already engaged and attached, and since it can be retrieved successfully through the funnel catheter with thrombus present, there is no deterrent to removing it. These are two major advantages of the current invention over prior art devices.

Additionally, to keep the device from becoming incorporated into the vena cava wall by cellular overgrowth, a drug eluting coating may be provided to the braid to inhibit the cellular response. This would be of advantage when the use of the current IVC filter invention is utilized over a medium to protracted term of several days to weeks. Another design that would diminish cellular overgrowth would be to apply an inert elastomeric covering over the portion of the IVC filter apparatus that contacts the vessel wall. This would essentially isolate the wires or members of the IVC filter from the vessel wall and prevent the cellular overgrowth from surrounding the wires and members of the filter. Alternatively, the membrane may comprise a drug that would also inhibit cellular response and act to further prevent any reaction by the body to the presence of the foreign object.

The placement of embodiments of the current invention with the features described above that limit the cellular response into the IVC prophylactically in patients who are to undergo major surgery, trauma patients, and other patients in whom there is a relatively high incidence of pulmonary embolism, but in which anticoagulation is contraindicated, would protect them from the threat of a potentially fatal pulmonary embolism. The device with the antiproliferative properties could be left in place for several weeks to months with a small guide wire exiting the venotomy site. The device could then be removed when the threat of pulmonary embolism has passed.

The elongated clot puller type device with wires extending for quite a distance proximally and distal to the expansile segment is designed to remove clot or thrombus physically from the veins and arteries and grafts and may be used subsequently to any less than completely successful lytic or pharmacomechanical therapy. It may also be used primarily instead of lytic or pharmacomechanical therapy. In the case of DVT involving the femoral or iliac veins, it consists of an elongated guide wire based device comprised of an inner and outer shaft with an expandable tubular braid, or other expansile means, in more or less its mid to caudal portion, and is inserted through the popliteal vein, through the clot in the femoral and/or iliac vein and the inserted tip left in place. The expandable tubular braid segment may comprise an elastomeric coating or covering and may have properties similar to the clot shredder described in the above paragraph. A funnel tipped catheter is inserted through the internal jugular vein, but may be inserted through the contralateral femoral vein or other vein. The funnel tip is placed adjacent to and cephalad to the end of the clot and the inserted tip of the guide wire based device. The guide wire based device tip is advanced into the funnel tip catheter and advanced further so that the inserted tip exits the hub of the funnel tipped catheter outside the body. The inserted tip is now free to be manipulated, advanced, and withdrawn through the hub of the jugular accessed funnel tipped catheter. A portion of the elongated guide wire component is still protruding from the venotomy in the popliteal space as it has not been advanced into the vein at this point. The inserted tip that has now exited the jugular venotomy through the funnel tipped catheter hub contains the inner and outer shaft ends and the operator can now expand and collapse the braid from the jugular access as well. The cephalic end of the guide wire based component is further withdrawn out of the funnel tipped catheter until the expansile section located in more or less the mid to proximal portion, or caudal portion, of the length of the device is advanced into the popliteal vein. Simply put, the expansile section is advanced into the popliteal vein by withdrawing the cephalic end of the device.

Once the expansile portion is within the popliteal vein, the cephalic end is manipulated so that the inner shaft is withdrawn with respect to the outer shaft causing the expansile section to deform from a tubular shape to a football or plate like shape. In these shapes, the expansile section is able to pull clot centrally from the popliteal and femoral vein (and from the iliac vein in the case of iliofemoral thrombosis) and into the funnel tipped catheter where continued traction and possible concomitant suction will remove the thrombus from the body. The degree of expansion of the expansile segment is manually controllable so that the expansile segment becomes smaller when it enters the funnel tipped catheter. Hence, the elongated clot puller may be utilized not only to pull clot into the catheter, but also to pull clot within the catheter to the hub and out the hub of the withdrawal catheter. Preferably, this guide wire based clot puller device is long enough so that even when the expansile structure nears or exits the external hub of the funnel tipped catheter, there is significant length of the caudal end of the device still protruding through the popliteal venotomy and available to be manipulated by the operator. Again, the device has two entrance/exit sites into the venous system and may be withdrawn/advanced from each of these ends. The expansile segment may be expanded/collapsed from only one end. The veins involved may be the popliteal, femoral, jugular, antecubital, or other veins, and the discussion herein is used for example only and not intended to limit the venotomy locations.

If a second pass through the popliteal and femoral vein is desired, then the expansile section is collapsed into a tubular shape by manipulating the inner and outer shafts of the cephalic end projecting from the hub of the catheter in the jugular venotomy, and the caudal end of the guide wire based device is withdrawn caudally out of the popliteal venotomy so that the collapsed expansile segment is drawn caudally through the funnel tipped catheter and caudally through the femoral and popliteal veins to a point within the popliteal vein just cephalad to the popliteal venotomy. The presence of ends of the elongated clot puller outside the body and the contractile and expansile features of the expansile component of the elongated clot puller will allow it to be repositioned from a point cephalad to the iliofemoral veins to the popliteal vein without the tedious process of navigating retrograde through the venous valves. Moreover the contractile and expansile features of the elongated clot puller will allow this repositioning to occur without damaging the valves.

Once the expansile segment is repositioned in the popliteal vein, the expansile segment is expanded again by withdrawing the inner shaft with respect to the outer shaft at the cephalic end, and the expanded expansile segment is withdrawn through the popliteal and femoral vein, pulling any remaining clot, thrombus, and fragments with it into the funnel tipped catheter where continued fraction and possibly suction will remove it from the body. This procedure of expanding the braid, pulling the clot, collapsing the braid, repositioning the expansile segment distally, and repeating the maneuver may be repeated any number of times if necessary. Collapsing the expansile segment is critical before it is repositioned in the popliteal vein as the venous valves would prevent easy passage caudally with the expansile segment expanded, causing damage to the venous valves. It is likely that only one or two passes will be needed to remove all of the thrombus, however.

After all of the thrombus has been removed, it may be advantageous to occlude the treated segment of vein cephalically with the funnel tipped catheter and instill an antiproliferative drug, such as paclitaxel, into the treated segment for at least a short period of time preferably from the popliteal approach. This would minimize any long term sequelae from the DVT or from the treatment that may result from cellular infiltration of the vein and the valves. Cellular infiltration of the valvular structure is a major reason they become stiff and nonfunctional, and the method of administration of this non proliferative agent after thrombus removal in the veins is novel and incorporated into this patent. The drug could be aspirated through the funnel tipped catheter, which is preferable, or released into the systemic circulation, and the entire device and components removed.

It may be advantageous to treat the clot to be removed with this device with a lytic agent for a period of time to soften it up so that it will more easily flow through the funnel tipped catheter. Because of the wires in the expandable expansile segment, the device will be able to scrape or displace clot that is adherent to the vessel wall, something that balloons are unable to do. Because the whole device is guide wire based, it occupies less annular space in the lumen of the funnel tipped collection catheter, thereby creating more room for the clot. This is also an advantage over balloon based thrombus removal and thrombus puller devices. These two features are critical in removing chronic, somewhat organized clot from the arteries and the veins.

The device in embodiments described herein may treat thrombus or clots that are spread or distributed in the vasculature as well as isolated thrombus or clots and combinations thereof.

In another embodiment of the venous disease treatment device, the device is configured with a percutaneous prosthetic venous valve. The human venous system in the lower extremities contains a number of one-way valves that function in allowing forward (antegrade) blood flow to the right atrium of the heart while preventing reverse (retrograde) flow to the feet. Using the muscle action of the calf, or the "peripheral heart," the body is able to overcome gravitational forces to maintain blood flow back to the heart. The valves thus prevent blood from pooling in the lower extremities. Physiologically functioning valves are capable of withstanding very high proximal pressure gradients with minimal leakage, and can open at very low distal pressure gradients. However, for many patients, venous function is severely compromised by chronic venous disease (CVD), caused by chronic venous insufficiency (CVI).

The primary objective of this embodiment is a clinically relevant functional prosthetic vein valve that is safe, effective, inexpensive, and easy to insert in the patient. It meets the necessary criteria of being biocompatible and low thrombogenicity, eliminates the problem of fibrin deposition, it opens to allow antegrade flow with very little resistance, and it prevents reflux and seals effectively allowing leakage of less than 1 ml/sec. It is also easily deliverable via standard catheter and guide wire techniques making the insertion an outpatient technique.

The instant embodiment provides an improved device for the delivery and placement of a prosthetic venous valve. In essence, the device combines a guide wire based detachable expansile structure with a valvular structure covering its distal portion. The device is constructed of an inner wire coaxially positioned within an outer sheath that slides relative to the inner wire. Coaxially placed over the inner wire, and distal to the distal end of the outer sheath, is an expansile mechanism that may be an annular expansile element. The ability to detach the expansile mechanism is accomplished, in one embodiment, by having the outer tube not bonded to the proximal end of the expanding element, and the inner wire of the support wire to be only slightly bonded to the distal end of the expanding element. In this case, the inner wire is pulled in a retrograde direction relative to the outer tube. This action causes the expanding element to expand radially. Once the expanding element expands to the desired shape for this particular application and is seated firmly against the inner wall of the vein, the inner wire is pulled out of the 'snap' or interference fit on the distal end of the expanding element and the expanded element with the valvular structure is left in place and both the inner and outer member of the support wire is removed from the body.

The device comprises a distal tip configured with device braid portion. When deployed, the braid portion imparts a minimal but effective level of axial force against the surrounding vessel of a patient so as to stabilize the device. The venous disease treatment device comprises an outer sheath coaxially placed over an inner sheath. The two sheaths are moveable relative to the each other serving to expand and collapse the expansile braid portion. When the braid is expanded, the inner sheath is advanced out from and away from the outer sheath causing the expansile braid portion to controllably engage the vessel wall. In this manner, the device may be very deliberately and accurately positioned, or re-positioned, against a vessel wall within a patient. The device braid portion may be self-expanding or it may be controlled by actuator sheaths. The braid expands to the vessel wall and stabilizes the device distal tip by contacting the vessel wall, essentially securing the device to the vessel wall by a gentle annular force.

The device would be inserted and removed into a patient in the undeployed configuration. The venous valve is folded around the braid portion to insert the preferred embodiment into the vein. The base of the venous valve stretches as the braid portion expands. The leaflets of the venous valve are closed as there is pressure in a more cepahlad direction that cause the leaflets to close. When the braid portion is deployed or extended, it may take a shape akin to a football shape. The braid portion is extended or deployed by withdrawing the inner shaft or sheath with respect to the outer shaft or sheath. The leaflets of the venous valve are open as there is flow from below allowing blood to flow through the venous valve in an antegrade manner.

The detachable feature is enabled by any of several means to include temporary or transient bonding/attachment of the braid portion to the outer sheath and temporary or transient bonding/attachment of the inner sheath to the device distal tip such that a first movement of the inner sheath away from distal tip serves to deploy the braid portion, and continued second movement of the inner sheath away from distal tip serves to severe the attachment/bonding of the inner sheath to the distal tip, thereby detaching the deployed braid portion and the venous valve. When employing the device in this manner, the remaining components of the device are then withdrawn from the patient, and the deployed braided portion would remain in the patient to serve, for example, as a prosthetic venous valve. The means to enable the detachable feature include, but are not limited to, interference fits of the braid portion and one or both of the outer sheath and/or to the device distal tip, separation as induced by differential thermal properties of the components and/or by connective components (not shown) that lose adhesive properties upon heating (for example, as caused by continued placement with a patient and/or against a vessel wall). Means may also be enabled through magnetic, electrical, mechanical, or other typical methods of providing temporary connections between components.

The expansile structure may be an annular braided element, an element comprised of spiral wires, a stent like structure, or the like. The critical action is for the expansile element to deform from a substantially tubular structure when inserted to a substantially plate like structure or even a football like structure when the inner wire is moved proximally with respect to the outer sheath in respect to the annular braided structure. In the case of a stent like structure, it may be a self expanding stent like structure or a balloon expandable stent like structure. This action will expand the expansile structure against the venous wall and secure the device in place. In any case, the number of wires or members forming the expansile structure may need to be minimized to allow unimpeded antegrade blood flow and to prevent thrombus formation. This can be controlled by choosing the size and number of wires in the braid and the pics per inch or density of the braid. A low density is preferred for this application. Alternatively, biodegradable wires or members made of polylactic acid, poly L lactide, or the like may be utilized in the expansile structure so that after placement and incorporation of the device into the venous wall by cellular overgrowth, the wires or members gradually dissolve and disappear. It is likely that both concepts, i.e., a minimal number of wires or members with a low density braid and use of biodegradable wires or members, will be incorporated into a preferred embodiment. Another alternative is to use a balloon on a separate catheter to compress the wires of the annular braided configuration radially and out of the lumen of the vessel to as to provide a channel through which blood may flow without any impediments.

Alternatively, the expansile structure may be a self expanding or balloon expandable stent like structure and, if so, only a few millimeters in length. In fact, a non proliferative drug coating may be applied to the expansile structure, whether it be a spiral wire type structure, an annular expansile structure, a stent like structure, or other construction. The biodegradable wires mentioned above may have a propensity to stimulate cellular overgrowth that may be deleterious and be problematic. The part of the expansile structure that contacts the vessel wall may be constructed of some other substance or, if constructed of a biodegradable wire, may be coated with a non proliferative agent to prevent cellular overgrowth.

In a preferred embodiment, the expansile structure is an expansile tubular structure that is encased in a special hydrogel that is approximately 90% water, so that it more closely emulates body fluids and soft tissue. In this configuration, the hydrogel would constitute the expansile securing structure and the valvular structure. The hydrogel would be the prosthetic valve, not a coating on the valve. Alternatively, some other supportive structure may be encased within the hydrogel, as the concept of expanding the device to fit the vein after delivery may take any one of several different configurations. Additionally, it may or may not have small barbs or some other mechanism to engage the venous wall to prevent migration.

The valvular structure may be a simple pliable and flexible duck bill like valve attached to a point near the mid portion of the expansile device, or near a point that corresponds to the largest circumference when the device is deployed. The flexibility and pliability features are needed to allow easy opening of the valve with very little pressure gradient and easy closing of the valve to prevent retrograde flow. Alternatively the valvular structure may be comprised of two or more flaps or sheets of material that fold onto each other in the closed state, but open easily to allow antegrade flow. While an elastomeric polymer may be used in a preferred embodiment, combining it with a hydrogel or some other substance may lessen the thrombogenicity, fibrin deposition, and possibility of infection. In fact, one hydrogel that may be utilized in the preferred embodiment is only 10% polymer. The hydrogel itself may comprise the valvular leaflet structure and not necessarily act as a coating as its properties of being 90% water would obviate the need for additional non proliferative, anti-bacterial, and other coatings.

The attachment of the valvular structure to the expansile structure deserves special mention as the base, or attached portion, of the leaflets must expand as the expansile structure changes from a tubular shape to a plate like shape, at least in a preferred embodiment. If the valve leaflets were constructed of an elastomeric polymer, a hydrogel, the special hydrogel mentioned above, or the like, the base of the valve leaflet would stretch with the radially expanding expansile structure when that structure is put in compression and changes from a more or less tubular structure to a more or less plate like structure. The stretching of the base of the leaflets would add some rigidity to the base of the leaflets which is advantageous and would give the leaflets some form. The free ends of the leaflets would be more flexible and pliable and able to open and close more easily. Moreover, because of the differences in flexibility created by this design, the venous pressures cephalad to the leaflets would tend to collapse the leaflets toward one another creating an effective seal.

The method of placement of the venous valve device in the common femoral or popliteal vein would entail pre-procedural evaluation with various imaging studies. Ultrasound of the anticipated site of placement with the patient standing for several minutes would measure the distended vein. It is anticipated that the chosen device would expand larger than the distended vein to insure proper delivery without subsequent migration or slippage of the device. While retrograde placement is possible, the preferred method would be to cannulate the popliteal vein and pass a catheter containing the guide wire based preferred embodiment to a chosen point in the common femoral vein. The catheter is then withdrawn somewhat, the device precisely positioned, and the expansile structure expanded within the vein. In the case of an annular expansile structure, the inner wire would be retracted or withdrawn in relationship to the outer sheath or member deforming the expansile structure against the vein wall. Further traction of the inner wire would cause the interference fit of the inner wire and the distal aspect of the expansile structure to slip, freeing the inner wire. The inner wire, outer sheath, and the insertion catheter are then removed, leaving the prosthetic valve consisting of the expansile structure and the valvular structure in place. Of course other mechanisms other than the expansile structure discussed herein may be utilized to affix the venous valve to the vein wall, including a stent like structure, an expanding ring like structure, or an expanding metal cage, and the like. The valve leaflets may be porcine valves attached to the supporting structure even.

The veins distend secondary to the venous hypertension that develops, causing the leaflets to be separate from each other and unable to coapt and close properly resulting in venous valvular insufficiency. One treatment is to apply a radiofrequency current or energy to the vein wall so that the scarring of the wall in a more or less circumferential manner causes the vein to contract. This is particularly effective if done just below (caudal) to the valve. It can be performed by the guide wire base braid structure. In this device, the braid contains a means or mechanism for delivering energy near the mid portion of the expanded braid. The braid is expanded against the vein wall, the radiofrequency, or other energy means to include heat, cold (ie thermal), chemical, is applied to the wall in a circumferential manner for a few seconds and the device removed. Subsequently the vein will contract because of scarring, allowing the vein leaflets to coapt and become competent again. Alternatively, a separate loop resembling a halo on a stem or other structure may be provided to deliver the energy. Ideally, this alternative loop assembly would be inserted without the full loop being expanded and, once inserted into the vessel, the loop expanded so that it contacts the venous wall circumferentially and then energy delivered through the stem or portion of the device supporting the loop.

While the detailed descriptions above are principally concerned with a tubular mesh braid as the device braid portion element that secures the device to the wall of the vessel, other device braid portion configurations that accomplish the same action are also feasible, including, but not limited to, stent like structures, parallel wires, non parallel wires, spiral elements, circular elements, malecots, tubular elements, laser cut structures, buddy wires, and any structure or component which expands near the distal tip of the device and secures it.

The expansile segment of the devices described above may be comprised of a tubular mesh braid preferably, but other configurations may also be used, such as a malecot and any one of a number of other expandable means.

The tubular members of the embodiments of the device may be formed of short segments of hypodermic tubing comprising a metal, metal alloy, or metal-polymer blend. Examples of suitable materials include stainless steel (e.g. type 304V), platinum, tungsten, nickel-titanium alloy, polyethylene terapthalate (PET), polytetraflouroethylene (PTFE), polyurethane (nylon) fluorinated ethylene propylene (FEP), polyurethane, polypropylene (PP), polyvinylchloride (PVC), polyether-ester, polyester, polyamide, elastomeric polyamides, block polyamide/ethers, polyether block amide (PEBA), silicones, polyethylene, polyetherether ketone (PEEK), polyimide (PI), and polyetherimide (PEI). The inner lumen of each tubular member may also include a lubricious coating such as polytetraflouroethylene (PTFE).

Optionally, thrombolytic agents can also be introduced through the device to help disrupt the thrombus and clot, and a vacuum and/or mechanical extraction system can be used to help transport the disrupted clot, thrombus, or other occlusive material through the catheter and out of the patient's body.

While the above description is concerned with DVT involving the lower extremities, the device and method may be employed in other veins, in grafts, and in arteries. In the arteries, there are no valves to deal with, but the procedure is otherwise similar. In fact, utilizing some components of the device to retrieve the fragments that frequently remain after prolonged thrombolysis in the arterial system would diminish the time and improve the results of the procedure in the arterial system as well in the venous system. This use in other systems is included by this reference.

In some embodiments of the device, the work element, for example the expansile braid mechanism, is positioned to face against the flow of blood, meaning that blood flows in the direction from the distal end or portion of the device toward the proximal end or portion of the device. For example, if the device were positioned in the inferior vena cava, the distal tip would be below, or caudal, and the proximal portion would be higher, or cephalic, with the blood flowing up from the leg to the device distal tip and past it toward the proximal portion.

In some embodiments, the particles captured, removed, and/or shredded by the device are of size ranging between 0.01 mm and 8 mm. In some embodiments, the particles, upon shredding, are reduced, along a substantially axial axis, to preferably between 0.02 mm and 2 mm, and most preferably between 0.1 mm and 1 mm.

In some embodiments, the work element of the device, for example the braid mechanism, engages the body channel, where engages means any one of touching with minimal radial force, pressing against the body channel to secure the device against, for example, movement caused by blood or fluid flow, and pressing against the body channel to prevent substantially all movement of the device.

In one embodiment, the device and all of its components are made of the same material. In another embodiment, the device and its components are made of different materials; for example, the inner and outer sheaths are made of one type of material and the braid is made of another material.

In one embodiment, the braid mechanism does not employ an inflatable balloon or similar structure that confines a fluid within a closed space to achieve a securing function.

In one embodiment, the braid is not a balloon as employed in catheters in the prior art that feature a balloon.

In one embodiment, the mesh braid is fitted with a membrane entirely impermeable to flow. Such an embodiment would be particularly useful as an occluder. Further, in such a configuration, the device would serve as both a securing catheter and a proximal embolic protection catheter.

In another embodiment, to further prevent movement or migration of the device during infusion, an attachment mechanism secured to the catheter shaft at or near the skin insertion site may be provided. It may vary in configuration from a suture attached to the tissues to a clip at the skin level to a securing device or to any other means of preventing movement of the catheter.

In one embodiment, the braid mechanism is configured with an adhesive mechanism to provide additional stability of the device. For example, the adhesive mechanism may comprise striations, gripping surfaces, or an adhesive material.

In one embodiment, the securing mechanism is configured with a mesh comprised of materials of variable strength to include a mesh with elastomeric elements and elastomeric longitudinal elements. Further, the mesh may be of various fabric materials.

In other embodiments, the braid of the device that secures the device to the wall of the vessel is accomplished through other means than a braided mesh structure, including, but not limited to, stent like structures, parallel wires, non parallel wires, spiral elements, circular elements, tubular elements, laser cut structures, buddy wires, a malecot device, and any structure or component which expands and secures the device. Further, the deployed or expanded braid portion may be of any shape that is extendable or deployable to engage a vessel wall and impart axial pressure against a vessel wall to include funnel shapes, umbrella shapes, conical shapes, and ring shapes.

Another aspect of various embodiments of the present invention includes providing device which is entirely or partially disposable. The outer sheath, inner sheath, and expansile securing element may comprise at least portions of biocompatible material which can stay in the vessel without impairing the final implantation. Alternatively, it may thus be a material that is resorbable, such as a resorbable polymer, in the vessel after the surgical procedure.

In another embodiment of the invention, the device is in communication via a conduit to enable electrical, hydraulic, pneumatic, or mechanical transmission (for example, through a wire). Such hydraulic communication allows, for example, remote or automated use of the device. Such mechanical communication allows, for example, the distal end to be maneuvered with further precision.

It is yet another aspect of the present disclosure to provide device that contains one or more detachable components. According to various embodiments, these detachable devices may include the expansile braid or, for example, a medical device for implantation, such as a stent.

Furthermore, the device may be configured to engage with other medical devices, such other medical devices to include other catheters.

One skilled in the art will appreciate that the ends, the braid, and other components of the device need not be limited to those specific embodiments described above. Other forms, shapes or designs that enable the foregoing aspects of the present invention are hereby incorporated into this disclosure. Forms, shapes and designs that relate to the provision of an end of a securing device fitted to a catheter to perform medical procedures are considered to be within the scope of the present disclosure.

One of ordinary skill in the art will appreciate that embodiments of the present disclosure may have various sizes. The sizes of the various elements of embodiments of the present disclosure may be sized based on various factors, including, for example, the anatomy of the patient, the person or other device operating the apparatus, the catheter insertion location, the size of operating site or the size of the surgical tools being used with the device.

One of ordinary skill in the art will appreciate that embodiments of the present disclosure may be constructed of materials known to provide, or predictably manufactured to provide, the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The venous disease treatment device elements could be flexible, semi-rigid, or rigid and made of materials such as stainless steel, titanium alloy, aluminum alloy, chromium alloy, and other metals or metal alloys. In certain embodiments, the device and/or particular components are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the device and/or particular components are made of a substantially transparent material and/or are rigidly opaque.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

This Summary of the Invention is neither intended nor should it be construed as being representative of the full extent and scope of the present disclosure. The present disclosure is set forth in various levels of detail in the Summary of the Invention, as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. Further, the drawings of the device do not detail all features of the device, and do not show the entire device, for example some drawings only detail the device end, and not the entire device length. Similar, some drawings do not detail the entire length of the channel involved, for example do not show the entire blood vessel length. It should be understood, of course, that the disclosure is not necessarily limited to the particular embodiments illustrated herein.

DETAILED DESCRIPTION

Figure 1:
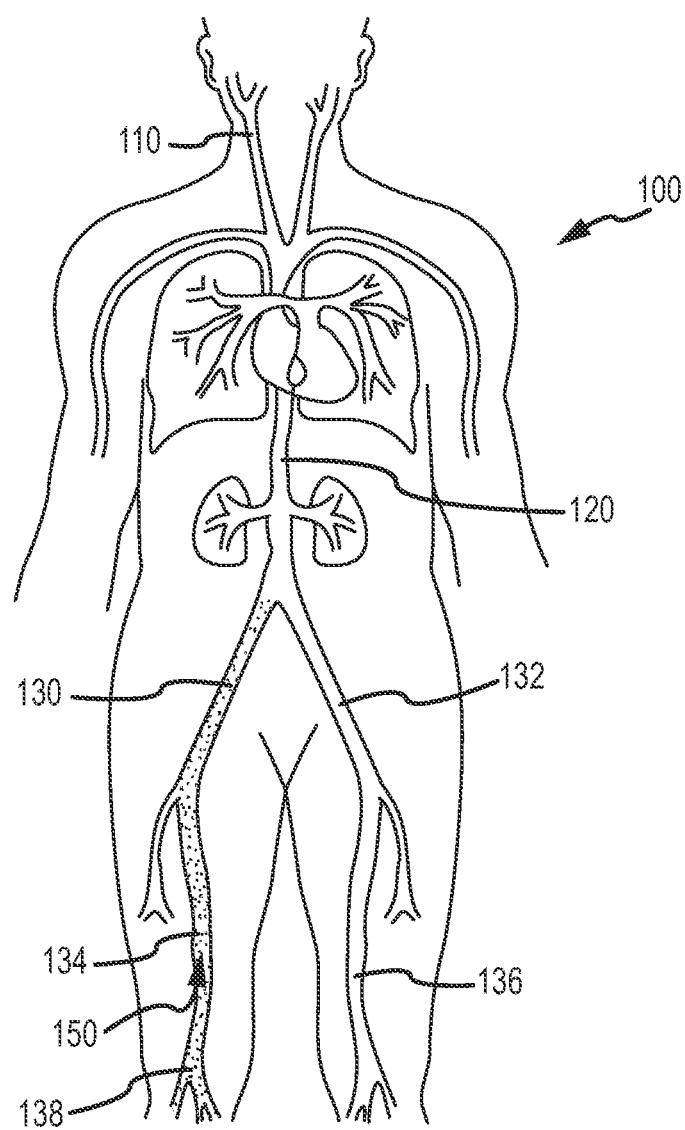
FIG. 1 schematically illustrates patient anatomy to include a thrombus.

The present invention relates to a medical device and method of use, and more specifically to a method and apparatus with coaxial components used to treat venous diseases.

The use of the instant inventions and methods are, in the case of venous disease, designed to treat Deep Vein Thrombosis by removing acute, subacute, and chronic thrombus, prevent pulmonary emboli, remove pulmonary emboli, prevent the smooth muscle cell migration and population into the valvular structure which causes valvular incompetence, repair damaged veins and venous valves, and to percutaneously place prosthetic venous valves.

An urgent need exists for minimal trauma devices and methods for capturing and/or completely removing blood clots from a patient's vasculature and for safely and effectively inserting prosthetic venous valves into a patient's vasculature. The present invention addresses these needs.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims.

Those of ordinary skill in the art will recognize a variety of equivalent variations on the description that follows. Like elements in various embodiments are commonly referred to with like reference numerals.

In order to provide greater clarity to the embodiments of the invention, a detailed description of the utility of the venous disease treatment device of the current invention is first provided. To achieve stability of the venous disease treatment device, a porous tubular mesh braid is attached to the distal aspect of the device in one embodiment. It may be a self expanding braid or it may be controlled by actuator sheaths which will be subsequently described. The braid expands to the vessel wall and stabilizes the device tip by contacting the wall, essentially securing it to the vessel wall by a gentle annular force. Example medical procedures detailed involve the capture, removal and shredding of thrombus. However, one of ordinary skill in the art will appreciate the concepts are transportable to most any other vessel. A utility is to accurately and reliably position the venous disease treatment device in the inferior vena cava of a patient, among other features.

Referring now to FIG. 1, the anatomy of a patient is shown.

In regard to FIG. 1, patient anatomy is schematically illustrated, with emphasis on a patient's venous system. FIG. 1 demonstrates organs and areas of interest within a patient 100, specifically the jugular vein 110, inferior vena cava 120, right external iliac vein 130, left external iliac vein 132, right femoral vein 134, left femoral vein 136, and popliteal vein 138. Of particular interest is the jugular vein 110, a typical insertion point for medical interventions involving the treatment of venous disease, and the inferior vena cava 120 and the right femoral vein 134 and left femoral vein 136, where clots or thrombus commonly develop. A thrombus 150 is shown distributed in the right femoral vein 134 and right external iliac vein 130. Although a distributed thrombus 150 in depicted in FIG. 1, the device according to embodiments described may also be used to treat isolated or concentrated thrombus 150 or clots. The treatment of venous disease requires the precise and reliable positioning of venous disease treatment devices, as enabled by this disclosure. As will be demonstrated subsequently, various embodiments of the current invention will secure a venous disease treatment device 200 within a patient 100 and overcome the technical problems described above when using the prior art devices and/or prior art methods of use. The inability to properly access a vascular area or lesion occurs in many of the other vessels shown in FIG. 1.

Referring now to FIGS. 2-5, several embodiments of the present invention are shown.

In regard to FIGS. 2-4, a venous disease treatment device 200 is shown comprising a device distal tip 220, a device inner sheath or tube 240, a device outer sheath or tube 250, and a device braid portion 260. A coupling element is provided for connecting the distal tip 220 of the device 200 to the inner sheath 240 and to the outer sheath 250. The device 200 is shown inserted within a vessel wall 290. The braid portion 260 connects to the outer sheath 250. The device 200 is configured to include a housing having a hollow interior and a closed distal tip 220. Each of the inner sheath 240 and the outer sheath 250 form lumens. Various work elements or mechanisms are mounted and movably disposed along the outer sheath 250 of the device 200. A work element connector is disposed in a lumen of the device body, preferably the axial lumen. FIGS. 2-4 detail a device braid portion 260 work element.

FIGS. 2-4 generally provides the venous disease treatment device 200 in one embodiment particularly suited to perform as an IVC filter. Alternatively it could represent an embodiment of the device suited to perform as a clot (or thrombus) puller and/or shredder.

Throughout this disclosure of the invention, "clot", "thrombus", and "particle" all reference any particulate targeted for medical intervention.

In the embodiment of FIGS. 2-4, when the work element or braid portion 260 of the device 200 is expanded, the inner sheath 240 is withdrawn out of and away from the outer sheath 250 causing the work element or braid portion 260 of the device 200 to expand. The two components inner sheath 240 and to the outer sheath 250 may be locked together by turning them or by other means, such as a locking mechanism (not shown). The device 200 may be utilized alone or may be delivered through a guide catheter to the vessel of interest. A companion guide catheter may in fact have the same or similar shape and features as the configuration demonstrated for the device 200 when used for infusion or delivery. A guide catheter, for example, may be secured cephalic, and the device 200 would pass coaxially through the guide catheter to, for example, to the inferior vena cava 120 region of FIG. 1. The device 200 may also be fitted with a guide catheter and/or funnel catheter 400 to thus operate as a substantially integrated unit or device.

Figure 2A:
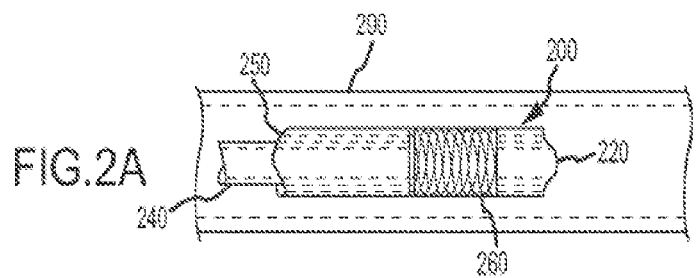
FIG. 2A provides a side view of one embodiment of the device inserted within a vessel of a patient including an inner sheath, outer sheath, distal tip, and unexpanded braid mechanism.
Figure 2B:
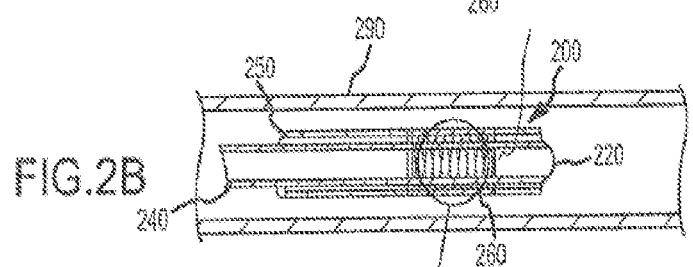
FIG. 2B provides a cross-sectional view of the device of FIG. 2A inserted within a vessel of a patient including an inner sheath, outer sheath, distal tip, and unexpanded braid mechanism.
Figure 2C:
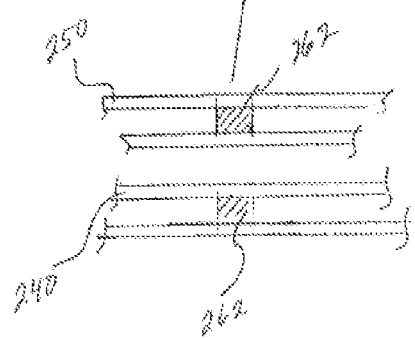
FIG. 2C provides a side view of the device of FIG. 2A inserted within a vessel of a patient including an inner sheath, outer sheath, distal tip, and expanded braid mechanism.
Figure 2C:
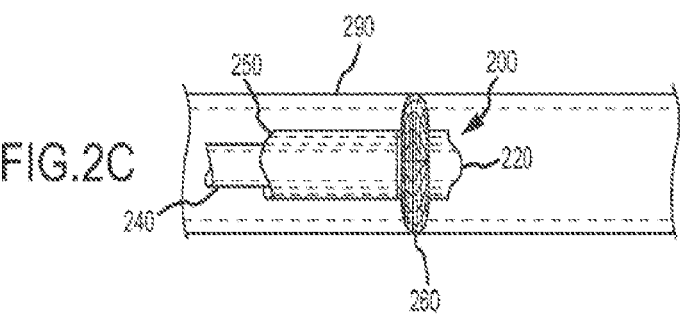
Figure 2D:
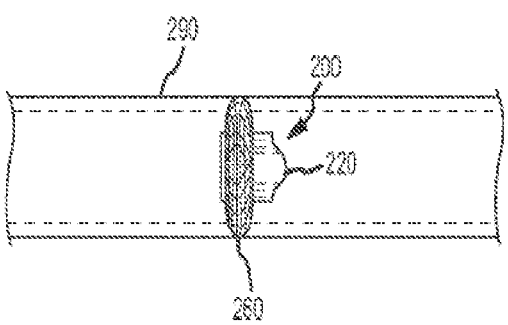
FIG. 2D provides a side view of the device of FIG. 2A inserted within a vessel of a patient including an inner sheath, outer sheath, distal tip, and expanded and detached braid mechanism.

Referring now in detail to FIGS. 2A-D, cross-sectional views of a venous disease treatment device 200 are provided with a distal tip 220 configured with device braid portion 260. When deployed, the braid portion 260 imparts a minimal but effective level of axial force against the surrounding vessel wall 290 of a patient 100 so as to stabilize the device 200. The venous disease treatment device 200 comprises an outer sheath 250 coaxially placed over an inner sheath 240. The two sheaths are moveable relative to each other serving to expand and collapse the expansile braid portion 260. FIGS. 2A-B depict the device 200 with the expansile braid portion 260 undeployed, a configuration utilized when the device is inserted into the patient 100. Further, FIGS. 2A-B depict the expansile braid portion 260 configured as a mesh braid. When the braid is expanded, as depicted in FIGS. 2C-D, the inner sheath 240 is withdrawn out from and away from the outer sheath 250 causing the expansile braid portion 260 to controllably engage the vessel wall 290. In this manner, the device may be very deliberately and accurately positioned, or re-positioned, against a vessel wall 290 within a patient 100. Herein the terms "expansile braid" and "mesh braid" and "braid" all reference the device braid portion 260. The device braid portion 260 may be a self-expanding or it may be controlled by actuator sheaths. The braid 260 expands to the vessel wall 290 and stabilizes the device 200 by contacting the vessel wall 290, essentially securing the device 200 to the vessel wall 290 by a gentle annular force.

In FIGS. 2A-B, the device braid portion 260 is attached to the outer or exterior of the outer sheath 250. The device 200 detailed in FIGS. 2A-B is shown with the braid portion 260 undeployed or unextended. The device 200 would be inserted and removed into a patient 100 in the undeployed configuration of FIGS. 2A-B. FIGS. 2C-D details the device 200 with the braid portion 260 deployed or extended. When the braid portion 260 is deployed or extended, it may take a shape akin to a football shape. The braid portion is extended or deployed by withdrawing the inner shaft or sheath 240 with respect to the outer shaft or sheath 250. The shape of the deployed braid portion 260 depicted in FIGS. 2C-D is a representative shape that the device 200 would assume when configured and employed to serve as an inferior vena cava (IVC) filter. Other shapes for the partially or fully deployed or expended braid 260 may be designed, to include but not be limited to oblong, spherical, toroid, and generally any substantially three-dimensional shape that substantially restricts passage of material, such as thrombus, from passing such a shape along or inside the vessel wall 290. A spacer 262 may be incorporated to limit the deformity of the braid portion 260 to the shape shown in FIGS. 2C-D and/or to prevent the braid 260 from deforming into a plate-like and/or planar shape. The deployed shape may also be substantially two-dimensional (e.g. a plate-like shape) if such a shape substantially restricts passage of material, such as thrombus, from passing along or inside the vessel wall 290.

The braid portion 260 configuration, to include but not be limited to, the braid portion 290 density, strand thickness, adhesiveness, and characteristics that influence the porosity or flow through the braid portion 260 can be varied to ensure adequate blood flow, but adequate trapping of venous emboli.

When the device 200 shown in FIGS. 2A-D was used during a thrombolytic procedure, the device 200 would be left in place, and for hours or even days after the procedure. Alternatively, the device 200 may be used when there is no thrombolytic procedure, but as protection against emboli in patients that cannot be anticoagulated because of surgery or other circumstances. In the configuration of the device shown in FIG. 2C, the braid portion 260 remains attached to the device outer sheath 250 and thus would have to eventually be removed.

In the embodiment of the device 200 shown in FIG. 2D, the deployed or extended braid portion 260 is detachable from the device 200, and thus would be permanently left in the patient 100. The detachable feature is enabled by any of several means, to include temporary or transient bonding/attachment of the braid portion 260 to the outer sheath 250 and temporary or transient bonding/attachment of the inner sheath 240 to the device distal tip 220, such that a first movement of the inner sheath 240 away from distal tip 220 serves to deploy the braid portion 260, and continued second movement of the inner sheath 240 away from distal tip 220 serves to sever the attachment/bonding of the inner sheath 240 to the distal tip 220, thereby detaching the deployed braid portion 260, as depicted in FIG. 2D. When employing the device 200 in this manner, the remaining components of the device 200 are then withdrawn from the patient 100, and the deployed braided portion 260 would remain in the patient 100, to serve, for example, as an IVC filter. The means to enable the detachable feature include, but are not limited to, interference fits of the braid portion 260 and one or both of the outer sheath 250 and/or to the device distal tip 220, separation as induced by differential thermal properties of the components and/or by connective components (not shown) that lose adhesive properties upon heating (for example, as caused by continued placement with a patient and/or against a vessel wall 290). Means may also be enabled through magnetic, electrical, mechanical, or other typical methods of providing temporary connections between components.

Other embodiments of the venous disease treatment device 200 include a clot/thrombus puller and a clot/thrombus shredder, as well as an occluder. Each of these embodiments are generally depicted in FIGS. 2-4, and vary based on the characteristics of the braid portion 260. More specifically, variations in the braid portion 260 configuration, to include but not be limited to, the braid portion 260 density, strand thickness, adhesiveness, diameter of strands, and other characteristics that influence the porosity or flow through the braid portion 260, and/or the ability of the braid 260 to capture and/or move a clot or thrombus. For example, a braid portion 260 that does not allow substantial flow, that is, a braid portion 260 that is substantially impermeable, would be employed as an occluder that may be used to occlude venous branches, for example. An occluder stops or blocks most if not all blood flow. Alternatively, a braid portion 260 configured with braids that allow larger clot particles to pass (than, for example, an IVC filter configuration) and that, when pulled into a thrombus would tend to substantially cut or break-up the thrombus, would be deemed a clot/thrombus shredder. An embodiment of the device 200 for use as a clot shredder would generally have braid portion 260 comprising a lower density of strands. In such a clot shredder embodiment, the thrombus fragments may be removed through a catheter or may be further dissolved with a thrombolytic catheter.

Further, a clot puller device 200 is generally depicted in FIGS. 2-4, and is different than the IVC filter configuration and/or the clot shredder configuration principally because of the characteristics of the braid portion 260. In the clot puller embodiment of the device 200, the components and the actions are similar to the clot shredder with movement of the inner shaft or sheath 240 with respect to the outer shaft or sheath 250 deforming the expansile braid portion segment 260 into a shape that engages the vessel wall 290. The expansile braid portion segment 260 may have a denser braid density (than the IVC embodiment and/or the clot shredder embodiment) and optionally an elastomeric covering to better pull clot material along the interior of the vessel and into a catheter, for example, for removal.

Figure 3A:
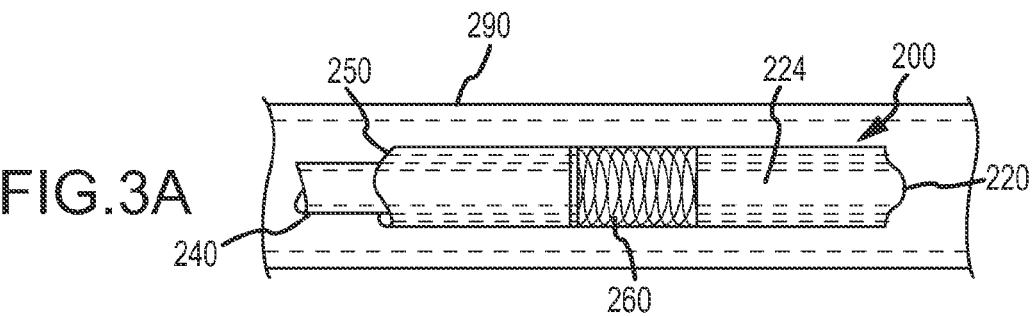
FIG. 3A provides a side view of another embodiment of the device with an extended distal portion inserted within a vessel of a patient including an inner sheath, outer sheath, distal tip, and unexpanded braid mechanism.
Figure 3B:
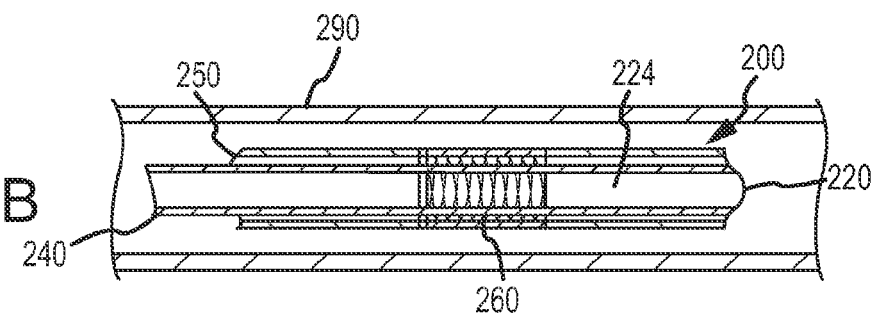
FIG. 3B provides a cross-sectional view of the device of FIG. 3A inserted within a vessel of a patient including an inner sheath, outer sheath, distal tip, and unexpanded braid mechanism.
Figure 3C:
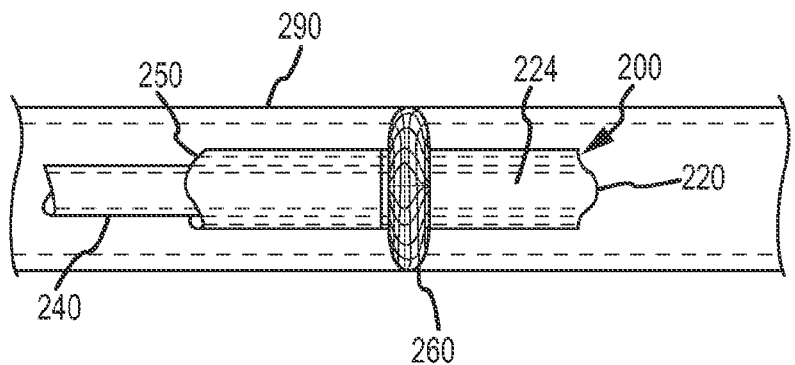
FIG. 3C provides a side view of the device of FIG. 3A inserted within a vessel of a patient including an inner sheath, outer sheath, distal tip, and expanded braid mechanism.

Referring now in detail to FIGS. 3A-C, a further embodiment of the device 200 is provided. FIGS. 3A-C provide cross-sectional views of a venous disease treatment device 200, similar to that of FIGS. 2A-C, except with the additional feature of an extended distal portion 224.

The device 200 comprises a distal tip 220 configured with device braid portion 260. When deployed, the braid portion 260 imparts a minimal but effective level of axial force against the surrounding vessel 290 of a patient 100 so as to stabilize the device 200. The venous disease treatment device 200 comprises an outer sheath 250 coaxially placed over an inner sheath 240. The two sheaths are moveable relative to each other serving to expand and collapse the expansile braid portion 260. FIGS. 3A-B depict the device 200 with the expansile braid portion 260 undeployed, a configuration utilized when the device is inserted into the patient 100. Further, FIGS. 2A-B depict the expansile braid portion 260 configured as a mesh braid. When the braid is expanded, as depicted in FIG. 3C, the inner sheath 240 is withdrawn out from and away from the outer sheath 250 causing the expansile braid portion 260 to controllably engage the vessel wall 290. In this manner, the device may be very deliberately and accurately positioned, or re-positioned, against a vessel wall 290 within a patient 100. The device braid portion 260 may be a self-expanding or it may be controlled by actuator sheaths. The braid 260 expands to the vessel wall 290 and stabilizes the device distal tip 220 by contacting the vessel wall 290, essentially securing the device 200 to the vessel 290 wall by a gentle annular force.

In FIGS. 3A-B, the device braid portion 260 is attached to the outer or exterior of the outer sheath 250. The device 200 detailed in FIGS. 3A-B is shown with the braid portion 260 undeployed or unextended. The device 200 would be inserted and removed into a patient 100 in the undeployed configuration of FIGS. 3A-B. FIG. 3C details the device 200 with the braid portion 260 deployed or extended. When the braid portion 260 is deployed or extended, it may take a shape akin to a football shape. The braid portion is extended or deployed by withdrawing the inner shaft or sheath 240 with respect to the outer shaft or sheath 250.

Figure 4A:
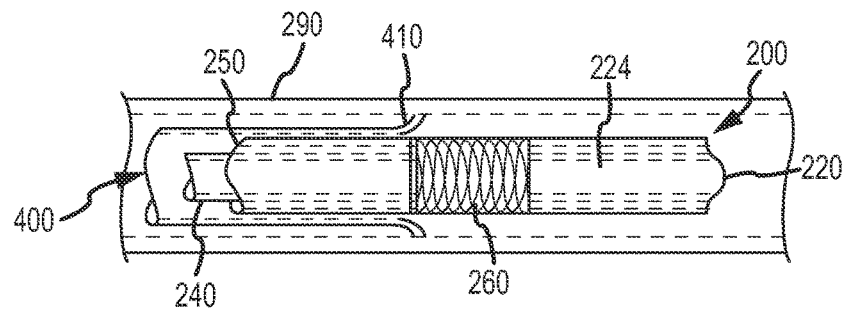
FIG. 4A provides a side view of the device of FIG. 3A with an extended distal portion inserted within a funnel catheter which in turn is inserted within a vessel of a patient.
Figure 4B:
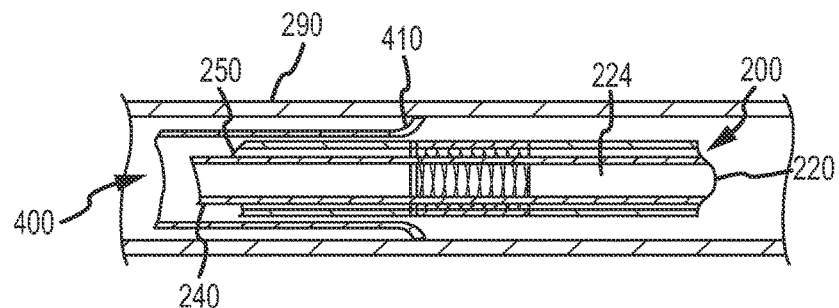
FIG. 4B provides a cross-sectional view of the device of FIG. 3A with an extended distal portion inserted within a funnel catheter which in turn is inserted within a vessel of a patient, wherein the braid mechanism is unexpanded.
Figure 4C:
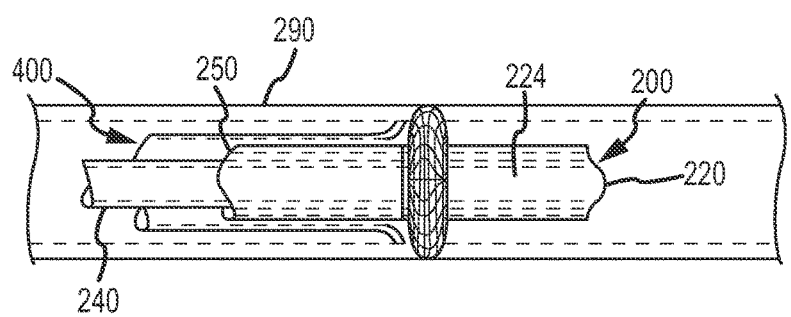
FIG. 4C provides a side view of the device of FIG. 3A with an extended distal portion inserted within a funnel catheter which in turn is inserted within a vessel of a patient, wherein the braid mechanism is expanded and wherein the funnel catheter and device braid portion are in contact with one another.

Referring now in detail to FIGS. 4A-C, the embodiment of the device 200 as depicted in FIGS. 3A-C is shown as deployed from within a traditional funnel catheter 400. The funnel catheter 400 includes a funnel distal tip 410 and funnel proximal tip 420.

Figure 5:
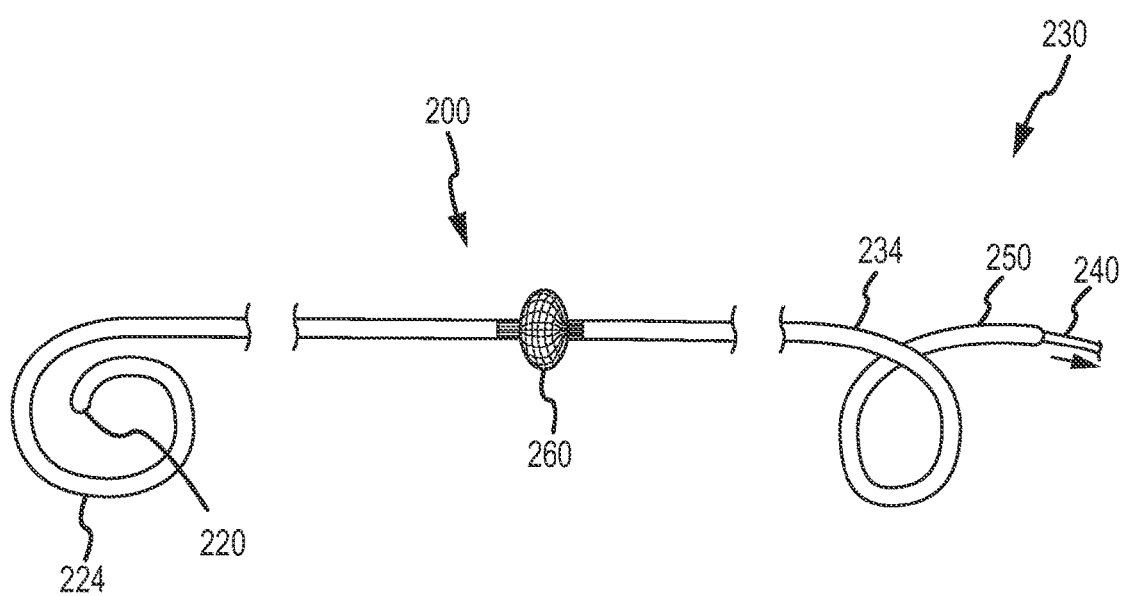
FIG. 5 provides a perspective view of another embodiment of the device with extended distal portion and extended proximal portion.

Referring now to FIG. 5, the device 200 generally of a similar embodiment to that depicted in FIGS. 3A-C is provided, yet with a particularly extended proximal portion 234 and with a particularly extended distal portion 224. In FIG. 5, the device 200 is also shown with device braid portion 260 extended or deployed, and with device distal tip 220, a device inner sheath or tube 240, and a device outer sheath or tube 250. The extended distal portion 224 may be configured so as to comprise a distal tip 220 that attaches to the inner sheath 240 (as shown in FIG. 5), or instead, may be a member attached to the distal tip 220, such as a wire. In the embodiment of FIG. 5, the length of the extended distal portion 224 is preferably between 50-200 cm in length, more preferably between 70-180 cm in length, and most preferably between 90-150 cm in length. The length of the extended distal portion 224 is such that the device 200 be manipulated from the popliteal vein 138 venotomy and from the jugular vein 110 venotomy.

It should be noted that the features of the embodiments of FIGS. 2-5 may be combined or adapted in any configuration to form embodiments not explicitly depicted or described.

Figure 6:
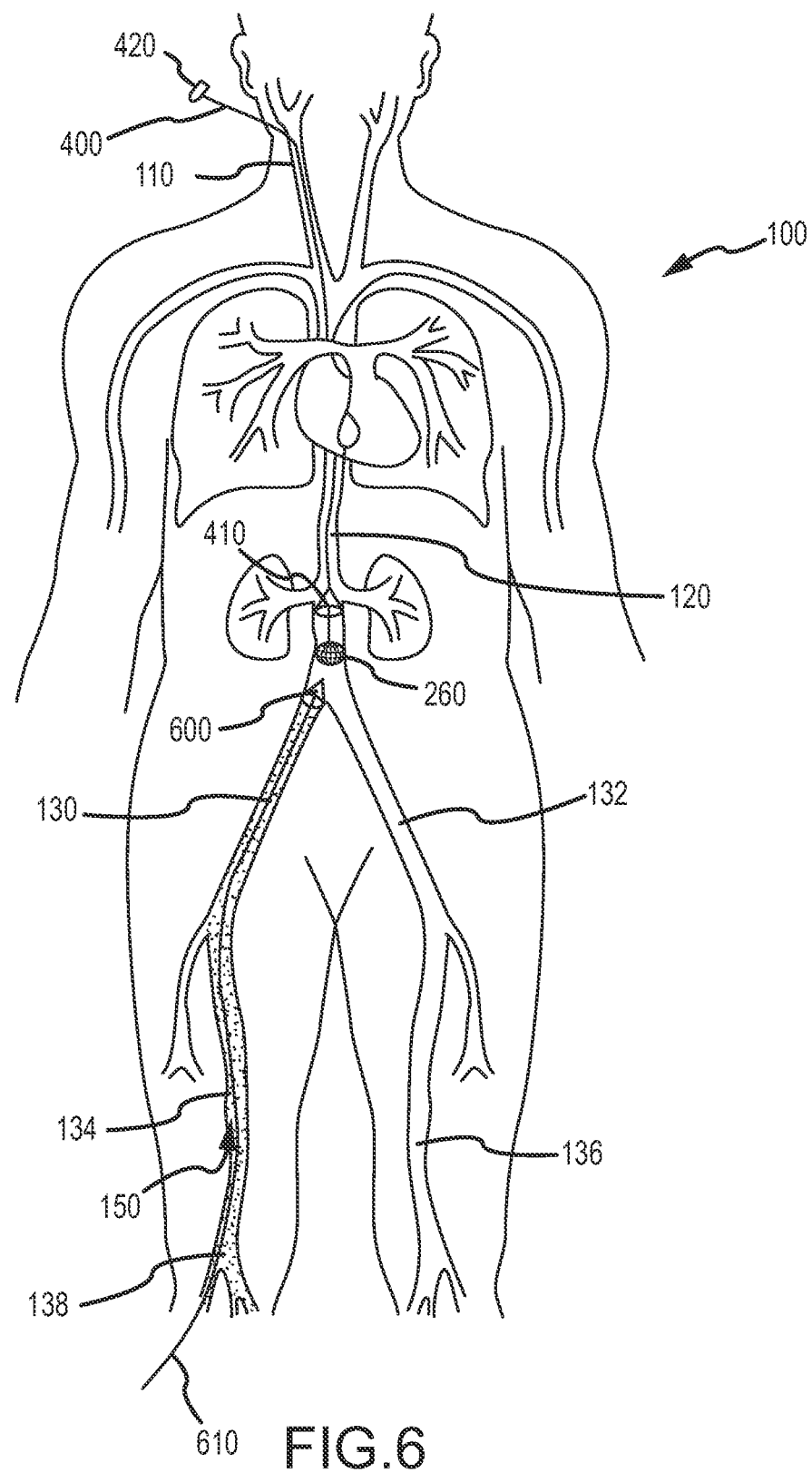
FIG. 6 schematically illustrates patient anatomy to include a thrombus and device inserted in patient.

Referring now to FIG. 6, a medical procedure to treat a thrombus 150 shown distributed in the right femoral vein 134 and right external iliac vein 130. Although a distributed thrombus 150 in depicted in FIG. 6, the device according to embodiments described may also be used to treat isolated or concentrated thrombus 150 or clots. A thrombolytic catheter 610 is positioned in the right femoral vein 134 and right external iliac veins 130, having entered the patient 100 through the popliteal vein 138. At the tip of the thrombolytic catheter 610 is an occluder 600. The device 200 is inserted into the patient 100 through the jugular vein 110. The embodiment of the device 200 of FIG. 6 is that of FIGS. 2A-C, and more specifically, configured as a procedural IVC filter. During insertion, the device 200 is configured as shown in FIGS. 2A-B, that is, the braid 260 is not deployed. The device 200 is inserted through a funnel catheter 400, as described in FIGS. 4A-B. Once positioned (here, in the inferior vena cava 120 region), the braid is deployed as shown in FIG. 2C. Proximal to the device 200, the device 200 in its IVC filter configuration with the braid portion 260 deployed, is a funnel tipped catheter 400 which may be used for retrieval or capture deployed braid portion 260, as shown in FIG. 4C. Note that the funnel tipped catheter 400 may not be present for most of the time the device 200, in its IVC filter configuration with the braid portion 260 deployed, is inserted into the patient 100. The device 200 in its IVC filter configuration with the braid portion 260 deployed will trap emboli (and other targeted particulates) that may occur during agitation of the thrombus 150 by the thrombolytic catheter 610. The device 200 in its IVC filter configuration with the braid portion 260 deployed may be removed through the funnel tipped catheter 400 whether the deployed braid portion 260 does or does not contain any clot or thrombus. The funnel tipped catheter 400 would make it easier to capture the device 200 in its IVC filter configuration with the braid portion 260 deployed and the clot or thrombus 150.

In an alternate method of use of the device 200 in the embodiment of FIGS. 2A-C, the device 200 is configured as either a clot shredder embodiment or a clot puller embodiment for DVT treatment. The device 200 is inserted into the patient 100 in the popliteal vein 138 in the configuration of FIGS. 2A-B. The device 200 is then expanded (into the configuration shown in FIG. 2C), and then the entire device 200 is withdrawn proximally up the vein. In the case of the clot shredder, the device 200 would slice through the clot. In the case of the clot puller, the device 200 would pull the clot along to be aspirated or gathered into a catheter.

Figure 7:
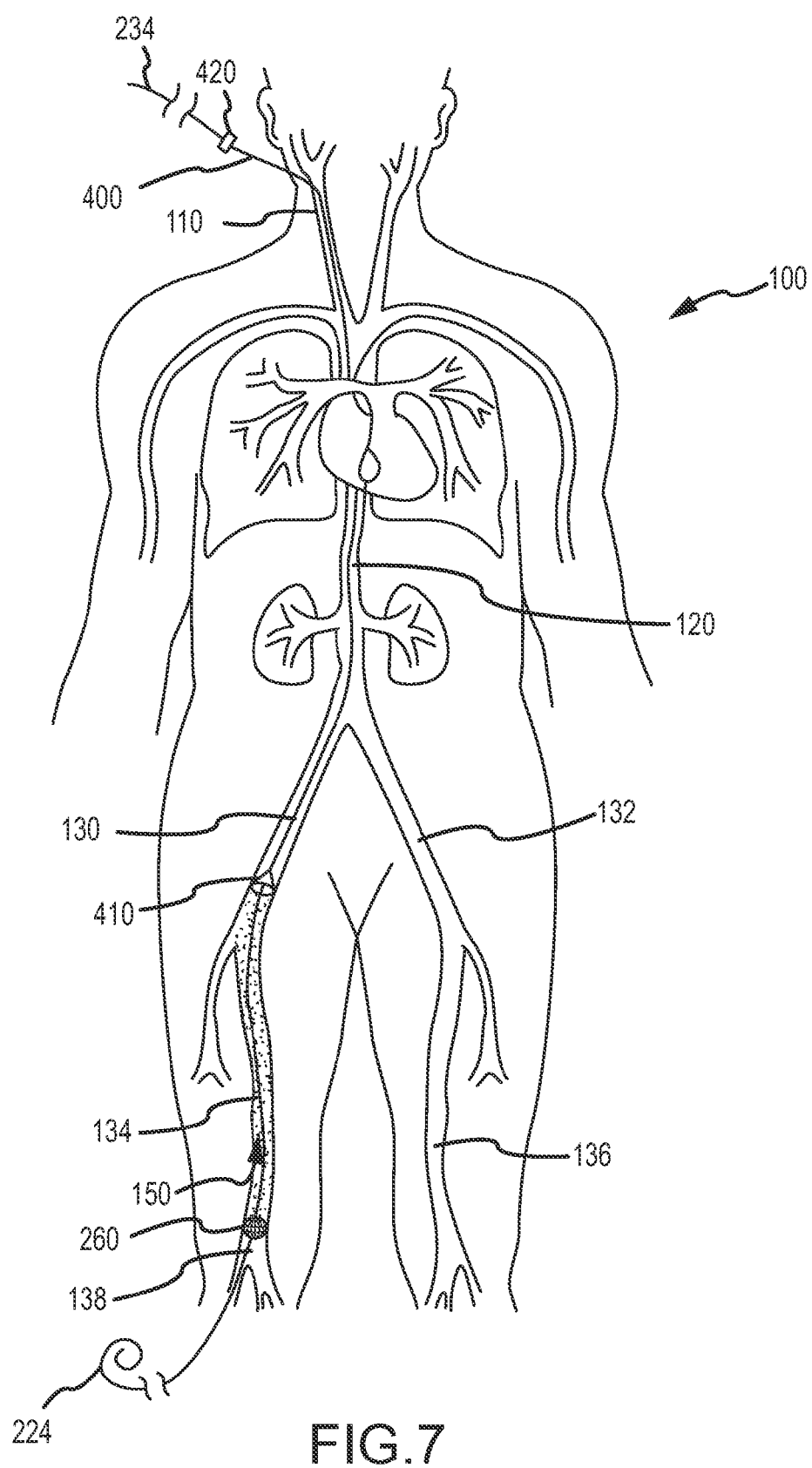
FIG. 7 schematically illustrates patient anatomy to include a thrombus and the device of FIG. 5 inserted in patient.

In another alternate method of use, provided as FIG. 7, of the device 200, the device 200 in the embodiment of FIG. 5 is employed. The device 200 of the embodiment of FIG. 5 is configured so as to be able to exit both the popliteal vein 138 and the jugular vein 110. In this configuration, the device 200 has an elongated cephalic (toward the head) portion with a proximal tip 230 and an elongated caudal (toward the tail) portion with distal tip 220. The extended distal portion 224 of the device 200 is positioned via Seldinger technique into the popliteal vein 138. During insertion, the device 200 is in the configuration of FIGS. 2A-B, that is with the braid portion 260 undeployed. The device is threaded through the thrombus 150 and into the mouth of the funnel tipped catheter 400 which has been inserted via the jugular vein 110. (Note that although a thrombus 150 is shown distributed in the right femoral vein 134 and right external iliac vein 130, the device according to embodiments described may also be used to treat isolated or concentrated thrombus 150 or clots). The device 200 is then advanced further so that its cephalic tip (i.e. proximal tip 230) exits the hub of the funnel tipped catheter 400 which protrudes from the jugular vein 110. The inner shaft, that is the device inner sheath 240 and the outer sheath 250, are then manipulated to deploy the braid portion 260. (The braid 260 is deployed as follows: the inner sheath 240 is withdrawn relative to the outer sheath 250, thereby causing the expansile braid segment 260 of the device 200 to deploy). The device 200 may be configured as any of the embodiments described, to include as an IVC filter, a clot shredder, or a clot puller. Once the braided portion 260 of the device 200 is deployed within the popliteal vein 138, the braided portion 260 expands to engage the vessel wall 290. Then, by withdrawing the cephalic end (that is, the device proximal tip 230) of the device 200, the braided portion 260 will pull thrombus 150 proximally into the funnel tipped catheter 400. When thrombus 150 is within the funnel tipped catheter 400, suction (not shown) may augment the traction of the thrombus 400 with the device 200. The device 200 is then withdrawn so that the braided portion 260 is just proximal to the hub of the funnel tipped catheter 400. If another pass through the venous system of the patient 100 to gather more thrombus 150 is desired, then the braided portion 260 is collapsed (i.e. unexpanded) into the configuration of FIG. 2A-B by withdrawing the inner sheath 240 relative to the outer sheath 250, repositioning the device 200 in the popliteal vein 138, re-deploying the braid portion 260, and repeating the above procedure.

Instead of advancing the elongated device through a funnel catheter, the free end of the device may be secured by a vascular snare and withdrawn out of the second entry site, either through a catheter or without a catheter. Having two ends of the device outside the body would give the operator the ability to place tension on the guide wire based structure so that other interventions such as angioplasty, stent placement, atherectomy, crossing of a chronic total occlusion, and the like could be performed.

Figure 8A:
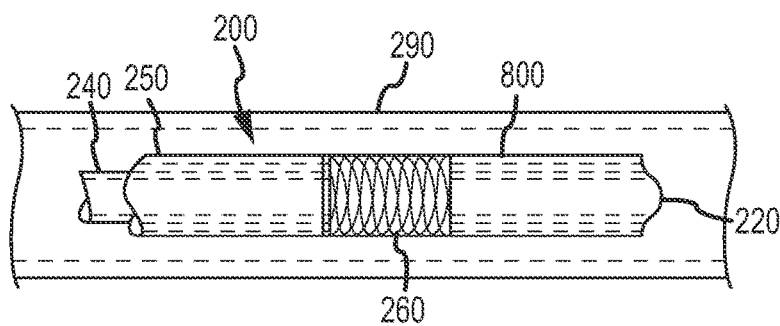
FIG. 8A provides a side view of another embodiment of the device inserted within a vessel of a patient, the device including an inner sheath, outer sheath, braid mechanism, and valvular structure, the braid mechanism unexpanded and the valvular structure unexpanded.
Figure 8B:
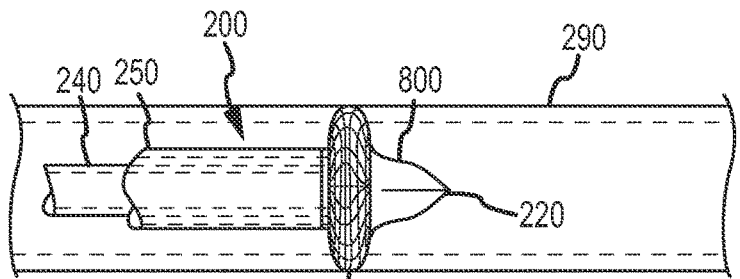
FIG. 8B provides a cross-sectional view of the device of FIG. 8A inserted within a vessel of a patient, the device including an inner sheath, outer sheath, braid mechanism, and valvular structure, the braid mechanism expanded and the valvular structure expanded.
Figure 8C:
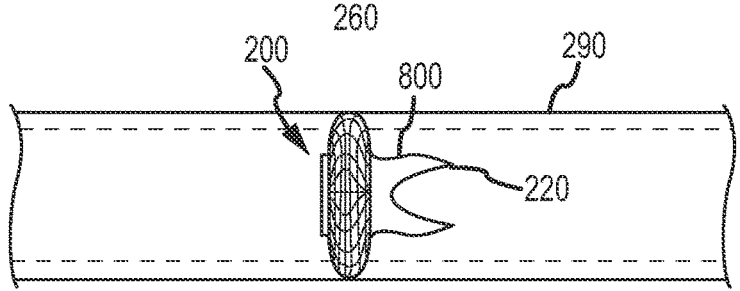
FIG. 8C provides a side view view of the device of FIG. 8A inserted within a vessel of a patient, the device including an inner sheath, outer sheath, braid mechanism, and valvular structure, the braid mechanism expanded and detached and the valvular structure expanded and detached.

Referring now in detail to FIGS. 8A-C, another embodiment of the device 200 is provided. FIGS. 8A-C provide cross-sectional views of a venous disease treatment device 200 configured with a percutaneous prosthetic venous valve 800. The device 200 comprises a distal tip 220 configured with device braid portion 260. When deployed, the braid portion 260 imparts a minimal but effective level of axial force against the surrounding vessel 290 of a patient 100 so as to stabilize the device 200. The venous disease treatment device 200 comprises an outer sheath 250 coaxially placed over an inner sheath 240. The two sheaths are moveable relative to the each other serving to expand and collapse the expansile braid portion 260. FIG. 8A depicts the device 200 with the expansile braid portion 260 undeployed, a configuration utilized when the device is inserted into the patient 100. Further, FIGS. 8A-C depict the expansile braid portion 260 configured as a mesh braid. When the braid is expanded, as depicted in FIGS. 8B-C, the inner sheath 240 is advanced out from and away from the outer sheath 250 causing the expansile braid portion 260 to controllably engage the vessel wall 290. In this manner, the device may be very deliberately and accurately positioned, or re-positioned, against a vessel wall 290 within a patient 100. The device braid portion 260 may be a self-expanding or it may be controlled by actuator sheaths. The braid 260 expands to the vessel wall 290 and stabilizes the device 200 by contacting the vessel wall 290, essentially securing the device 200 to the vessel 290 wall by a gentle annular force. In FIGS. 8A-C, the device braid portion 260 is attached to the outer or exterior of the outer sheath 250.

The device 200 detailed in FIG. 8A is shown with the braid portion 260 undeployed or unextended. The device 200 would be inserted and removed into a patient 100 in the undeployed configuration of FIG. 8A. The venous valve 800 is folded around the braid portion 260 in the configuration of FIG. 8A to insert the preferred embodiment into the vein. FIG. 8B details the device 200 with the braid portion 260 deployed or extended. The base of the venous valve 800 stretches as the braid portion 260 expands. The leaflets of the venous valve 800 are closed as there is pressure in a more cepahlad direction (here, to the left) that cause the leaflets to close. When the braid portion 260 is deployed or extended, it may take a shape akin to a football shape. The braid portion is extended or deployed by withdrawing the inner shaft or sheath 240 with respect to the outer shaft or sheath 250. FIG. 8C details the device 200 with the braid portion 260 deployed or extended, the venous valve 800 detached, and the venous valve 800 open. The leaflets of the venous valve 800 are open as there is flow from below (from the left to the right) allowing blood to flow through the venous valve 800 in an antegrade manner (from the left to the right). In the case in which the expansile portion comprises a stent like structure (not shown) to secure the valve to the vessel wall, the stent like structure may be self expanding or may be balloon expandable. In the embodiment of the device 200 shown in FIG. 8C, the deployed or extended braid portion 260 and the venous valve 800 is detachable from the device 200, and thus would be permanently left in the patient 100. The detachable feature is enabled by any of several means, to include temporary or transient bonding/attachment of the braid portion 260 to the outer sheath 250 and temporary or transient bonding/attachment of the inner sheath 240 to the device distal tip 220, such that a first movement of the inner sheath 240 away from distal tip 220 serves to deploy the braid portion 260, and continued second movement of the inner sheath 240 away from distal tip 220 serves to severe the attachment/bonding of the inner sheath 240 to the distal tip 220, thereby detaching the deployed braid portion 260 and the venous valve 800, as depicted in FIG. 8C. When employing the device 200 in this manner, the remaining components of the device 200 are then withdrawn from the patient 100, and the deployed braided portion 260 would remain in the patient 100, to serve, for example, as a prosthetic venous valve. The means to enable the detachable feature include, but are not limited to, interference fits of the braid portion 260 and one or both of the outer sheath 250 and/or to the device distal tip 220, separation as induced by differential thermal properties of the components and/or by connective components (not shown) that lose adhesive properties upon heating (for example, as caused by continued placement with a patient and/or against a vessel wall 290). Means may also be enabled through magnetic, electrical, mechanical, or other typical methods of providing temporary connections between components.

While the detailed descriptions above are principally concerned with a tubular mesh braid as the device braid portion 260 element that secures the device 200 to the wall of the vessel 290, other device braid portion 260 configurations that accomplish the same action are also feasible, including, but not limited to stent like structures, parallel wires, non parallel wires, spiral elements, circular elements, malecots, tubular elements, laser cut structures, buddy wires, and any structure or component which expands near the distal tip of the catheter and secures it while preserving flow is included by this mention.

To provide further clarity to the Detailed Description provided herein in the associated drawings, the following list of components and associated numbering are provided:
Ref. No. Component
100 Patient
110 Jugular vein
120 Inferior vena cava
130 Right external iliac vein
132 Left external iliac vein
134 Right femoral vein
136 Left femoral vein
138 Popliteal vein
150 Thrombus
200 Device
220 Device distal tip
224 Device extended distal portion
230 Device proximal tip
234 Device extended proximal portion
240 Device inner sheath
250 Device outer sheath
260 Device braid portion
290 Vessel wall
400 Funnel catheter
410 Funnel catheter distal tip
420 Funnel catheter proximal tip
600 Occluder
610 Thrombolytic catheter
800 Venous Valve While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A venous treatment apparatus comprising:
   a device comprising an inner sheath and an outer sheath, the outer sheath having a proximal portion, an extended distal portion having a length between 50 cm and 400 cm, and a central portion and the inner sheath substantially fitting within the outer sheath,
   said central portion of the outer sheath including an expansile braid mechanism having a distal end connected to the extended distal portion of the outer sheath and having a proximal end connected to the proximal portion of the outer sheath,
   said expansile braid mechanism deployable by axial movement of said inner sheath within said outer sheath so as to engage said central portion against a venous vessel when said venous treatment apparatus is inserted within said venous vessel in a manner that positions said expansile braid mechanism,
   said expansile braid mechanism being at least partially porous to thrombus and comprising woven strands having one or more of a weave pattern density, strand thickness, adhesiveness, or strand diameter, such that, upon contact with said thrombus, the expansile braid mechanism substantially breaks the thrombus into particles.

2. The apparatus according to claim 1, wherein said expansile braid mechanism is detachable.

3. The apparatus according to claim 1, wherein said expansile braid mechanism is configured to substantially capture particles within said venous vessel.

4. The apparatus according to claim 1, wherein said device has a mechanism to deliver to the venous vessel at least one of a medicament and a fluid.

5. The apparatus according to claim 1, wherein said expansile braid mechanism is configured to occlude flow within said venous vessel.

6. The apparatus according to claim 1, wherein said expansile braid mechanism is configured to substantially break the thrombus particles to an axial dimension at or below 2 mm within said venous vessel.

7. The apparatus according to claim 1, wherein said expansile braid mechanism is configured to substantially remove particles within said venous vessel.

8. The apparatus according to claim 1, wherein said expansile braid mechanism further comprises an elastomeric coating.

9. The apparatus according to claim 1, further comprising a spacer tube coaxially fitted over said inner sheath that inhibits deformity of said expansile braid mechanism.

10. The apparatus according to claim 1, wherein said extended distal portion has a length of between 50 cm to 200 cm.

11. The apparatus according to claim 1, wherein said extended distal portion has a length of between 70 cm to 180 cm.

12. The apparatus according to claim 1, wherein said extended distal portion has a length of between 90 cm to 150 cm.

13. A venous treatment apparatus comprising:
    a device comprising an inner sheath and an outer sheath, the outer sheath having an extended proximal portion, an extended distal portion having a length between 50 cm and 400 cm, and a central portion and the inner sheath substantially fitting within the outer sheath,
    said central portion of the outer sheath including an expansile braid mechanism having a distal end connected to said extended distal portion of the outer sheath and having a proximal end connected to said proximal portion of the outer sheath, said expansile braid mechanism deployable by axial movement of said inner sheath within said outer sheath so as to engage said central portion against a venous vessel when said venous treatment apparatus is inserted within said venous vessel in a manner that positions said expansile braid mechanism, wherein said extended distal portion is configured to be inserted from a first vascular entry access site and exit from a second vascular entry access site, and wherein an overall length of said device is sufficient to allow user manipulation of said inner sheath and said outer sheath from either or both access sites.

14. The apparatus according to claim 13, wherein said first vascular entry access site is selected from the group consisting of: the jugular vein, the femoral vein, the subclavian vein, and the axillary vein; and the second vascular entry access site is the popliteal vein.

15. The apparatus according to claim 13, wherein the extended distal portion is selected from the group consisting of: an annular expansile element, a stent-like structure, a spiral wire-like structure, and a guide wire.

16. The apparatus according to claim 15, wherein said extended distal portion is substantially covered by a hydrogel.

17. The apparatus according to claim 13, wherein said extended distal portion has a length of between 70 cm to 200 cm.

18. The apparatus according to claim 13, wherein said extended distal portion includes a distal tip configured to be inserted into a funnel tipped catheter in said venous vessel.

19. A method of treating a target site within a venous vessel through which fluid flows, comprising:

a) providing a venous treatment apparatus comprising a device comprising an inner sheath and an outer sheath, the outer sheath having a proximal portion, an extended distal portion having a length between 50 cm and 400 cm, and a central portion and the inner sheath substantially fitting within the outer sheath, said central portion of the outer sheath further having an expansile braid mechanism having a distal end connected to said extended distal portion of the outer sheath, b) deploying said expansile braid mechanism by axially moving said inner sheath within said outer sheath so as to expand a diameter of said braid mechanism so that said diameter contacts a venous vessel; and c) translating said expansile braid mechanism in said venous vessel to contact thrombus therein and to break apart the thrombus into particles.

20. The method according to claim 19 further comprising positioning a funnel catheter in said venous vessel, and wherein breaking-apart particles comprises drawing the expansile braid mechanism toward said funnel catheter and cutting said particles with said expansile braid mechanism.

* * * * *